United States Patent
Burton et al.

(10) Patent No.: US 11,864,986 B2
(45) Date of Patent: *Jan. 9, 2024

(54) METHOD AND APPARATUS FOR FIXATION OF IMPLANTABLE DEVICE FOR URINARY CONTINENCE

(71) Applicant: Uromedica, Inc., Plymouth, MN (US)

(72) Inventors: John H. Burton, Minnetonka, MN (US); Timothy C. Cook, Wayzata, MN (US)

(73) Assignee: Uromedica, Inc., Plymouth, MN (US)

( * ) Notice: Subject to any disclaimer, the term of this patent is extended or adjusted under 35 U.S.C. 154(b) by 169 days.

This patent is subject to a terminal disclaimer.

(21) Appl. No.: 17/302,533

(22) Filed: May 5, 2021

(65) Prior Publication Data

US 2021/0393387 A1 Dec. 23, 2021

Related U.S. Application Data

(63) Continuation of application No. 16/949,991, filed on Nov. 23, 2020.

(60) Provisional application No. 63/042,947, filed on Jun. 23, 2020.

(51) Int. Cl.
| | | |
|---|---|---|
| *A61F 2/00* | (2006.01) | |
| *A61M 25/01* | (2006.01) | |
| *A61M 25/10* | (2013.01) | |

(52) U.S. Cl.
CPC ....... *A61F 2/0027* (2013.01); *A61M 25/0102* (2013.01); *A61M 25/10182* (2013.11)

(58) Field of Classification Search
CPC ............. A61F 2/0027; A61M 25/0102; A61M 25/10182; A61N 5/10; A61N 5/1001; A61N 5/1002; A61N 5/1014; A61N 5/1015; A61N 5/1027; A61N 2005/1003; A61N 2005/1004; A61N 2005/1005
See application file for complete search history.

(56) References Cited

U.S. PATENT DOCUMENTS

| | | | |
|---|---|---|---|
| 4,924,881 A | | 5/1990 | Brewer |
| 4,936,823 A | * | 6/1990 | Colvin ................. A61N 5/1002 600/7 |

(Continued)

OTHER PUBLICATIONS

"International Application Serial No. PCT US2021 070512, International Search Report dated Sep. 15, 2021", 8 pages.

(Continued)

*Primary Examiner* — Samuel G Gilbert
(74) *Attorney, Agent, or Firm* — Schwegman Lundberg & Woessner, P.A.

(57) ABSTRACT

An implantable device includes a conduit, an adjustable membrane element coupled to the conduit near the front end of the conduit for controllable coaptation of a body lumen, such as coaptation of a urethra as treatment for urinary incontinence, and a fixation mechanism at or near the front end of the conduit. In various embodiments, the fixation mechanism can anchor the implantable device to the tissue using a movement of a push wire. Optionally, the fixation mechanism can also allow the implantable device to be released from the tissue using another movement of the push wire, to allow for re-positioning or removal of the implantable device.

21 Claims, 19 Drawing Sheets

(56) References Cited

U.S. PATENT DOCUMENTS

| | | | |
|---|---|---|---|
| 5,938,582 A * | 8/1999 | Ciamacco, Jr. | A61N 5/1002 600/3 |
| 5,964,806 A | 10/1999 | Cook et al. | |
| 6,045,498 A | 4/2000 | Burton et al. | |
| 6,315,789 B1 | 11/2001 | Cragg | |
| 6,419,624 B1 | 7/2002 | Burton et al. | |
| 6,579,224 B1 | 6/2003 | Burton et al. | |
| 7,212,870 B1 | 5/2007 | Helland | |
| 7,493,175 B2 | 2/2009 | Cates et al. | |
| 8,543,224 B2 | 9/2013 | Foster et al. | |
| 8,747,417 B2 | 6/2014 | Truong | |
| 8,812,134 B2 | 8/2014 | Foster et al. | |
| 8,926,494 B1 | 1/2015 | Cook et al. | |
| 9,775,982 B2 | 10/2017 | Grubac et al. | |
| 10,376,690 B2 | 8/2019 | Grubac et al. | |
| 10,391,306 B2 | 8/2019 | Ma et al. | |
| 2005/0256364 A1 | 11/2005 | Burton et al. | |
| 2010/0261951 A1 | 10/2010 | Cook et al. | |
| 2010/0292530 A1 * | 11/2010 | Cook | A61M 25/0017 600/30 |
| 2012/0108881 A1 * | 5/2012 | Chi Sing | A61N 5/1002 600/3 |
| 2012/0165600 A1 | 6/2012 | Vitzthum | |
| 2012/0172690 A1 | 7/2012 | Anderson et al. | |
| 2013/0325110 A1 | 12/2013 | Khalil et al. | |
| 2017/0042549 A1 | 2/2017 | Kaplan et al. | |
| 2019/0083801 A1 | 3/2019 | Yang et al. | |
| 2020/0054883 A1 | 2/2020 | Eby et al. | |
| 2020/0261200 A1 | 8/2020 | Cook et al. | |

OTHER PUBLICATIONS

"International Application Serial No. PCT US2021 070512, Written Opinion dated Sep. 15, 2021", 7 pages.

U.S. Appl. No. 16/949,991, filed Nov. 23, 2020, Method and Apparatus for Fixation of Implantable Device for Urinary Continence.

"U.S. Appl. No. 16/949,991, Non Final Office Action dated Dec. 21, 2022", 14 pgs.

"International Application Serial No. PCT US2022 076348, International Search Report dated Dec. 20, 2022", 7 pgs.

"International Application Serial No. PCT US2022 076348, Written Opinion dated Dec. 20, 2022", 7 pgs.

"International Application Serial No. PCT US2021 070512, International Preliminary Report on Patentability dated Jan. 5, 2023", 9 pgs.

* cited by examiner

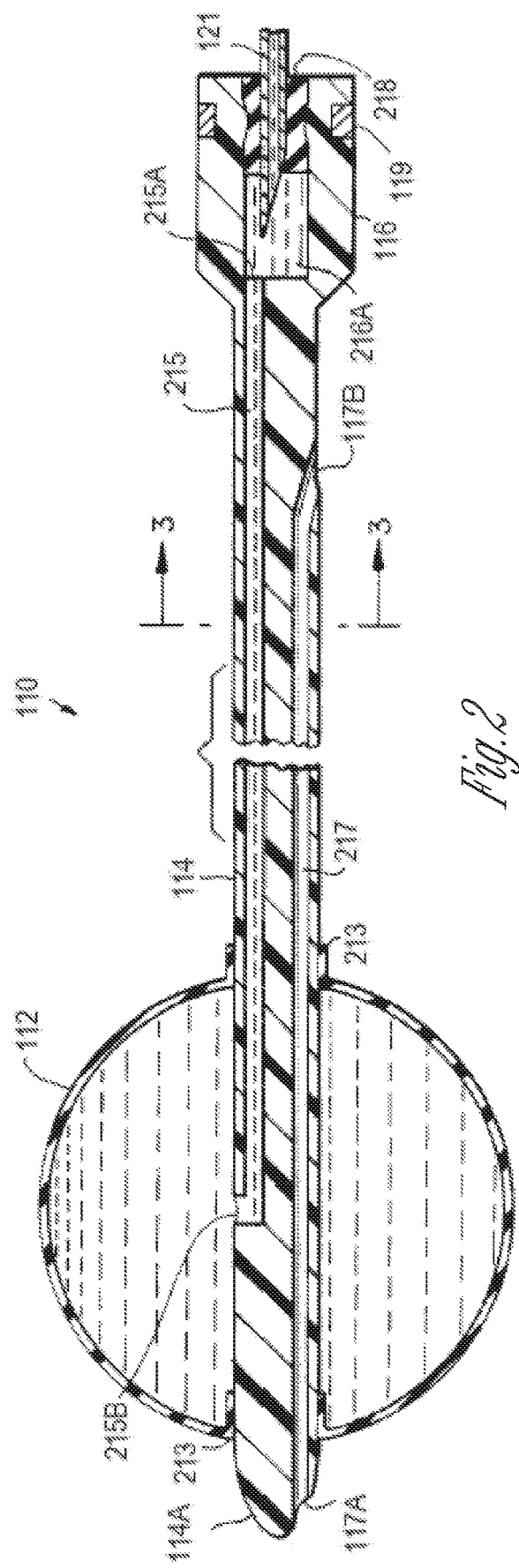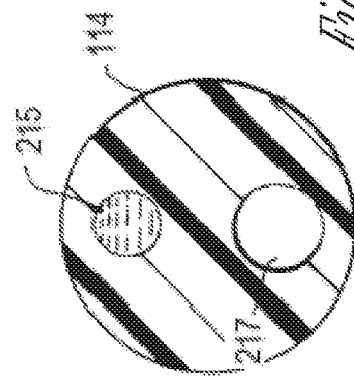

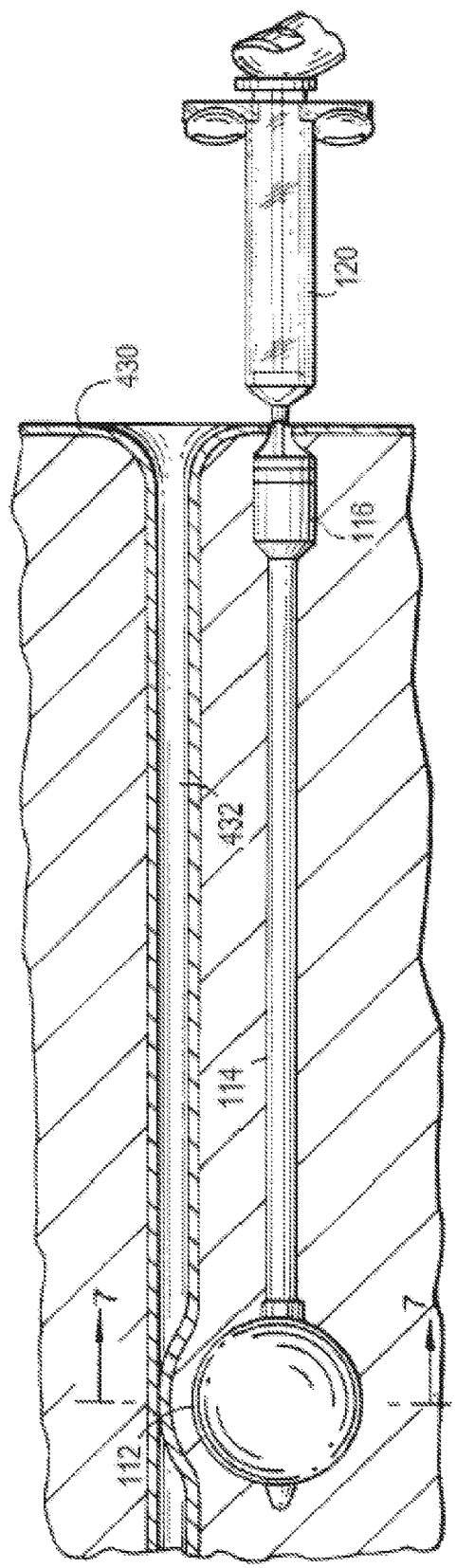
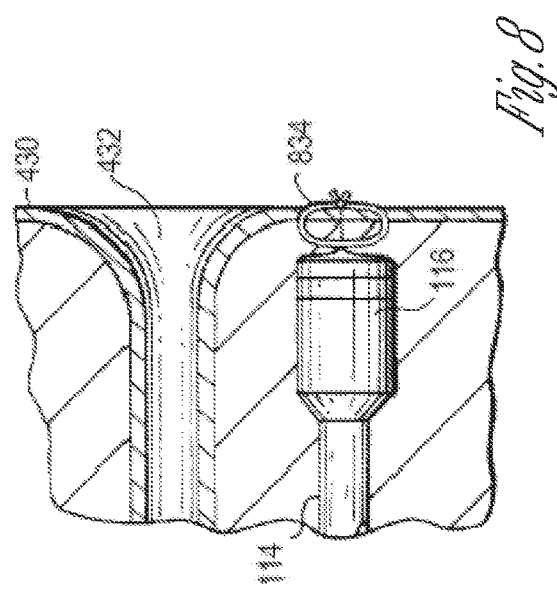
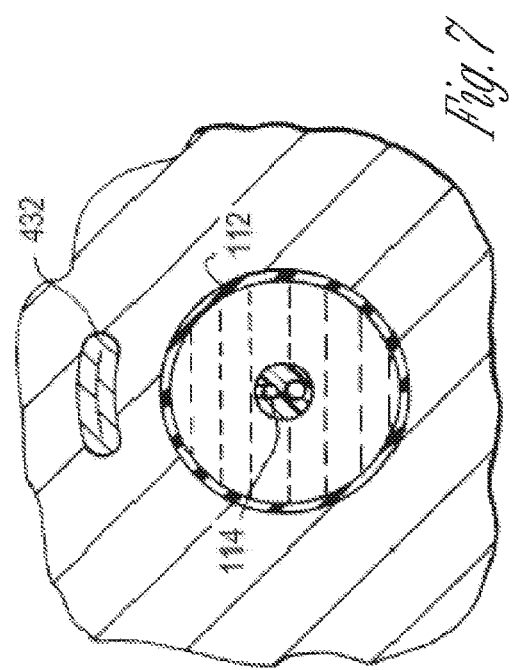

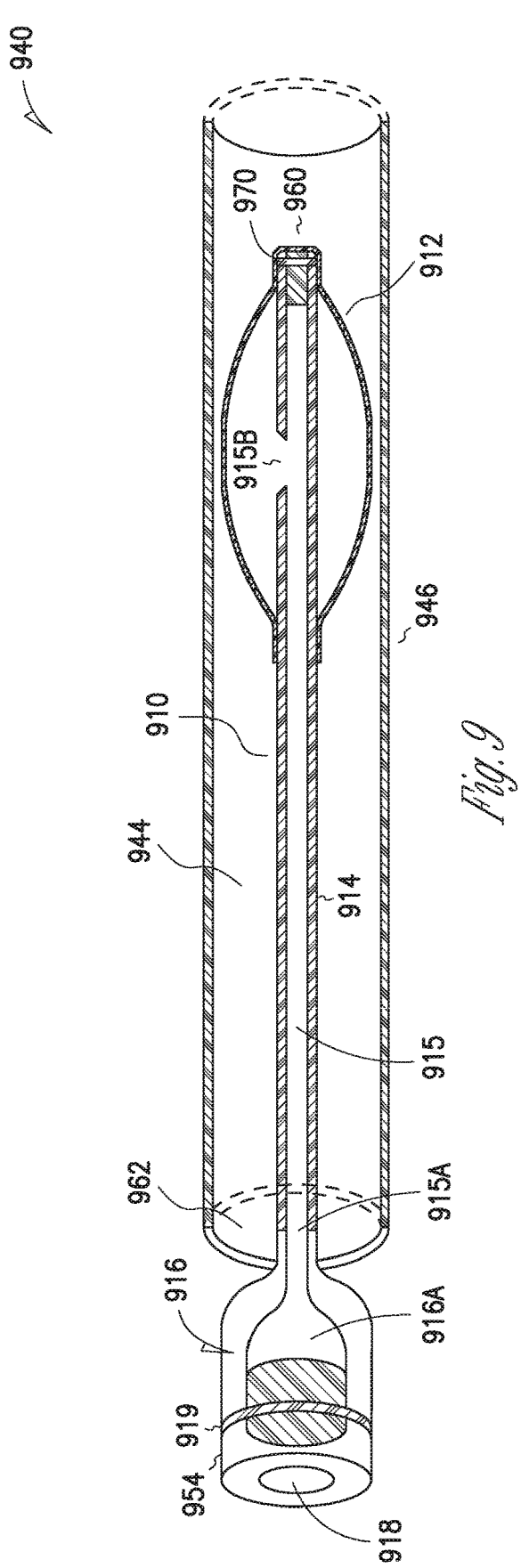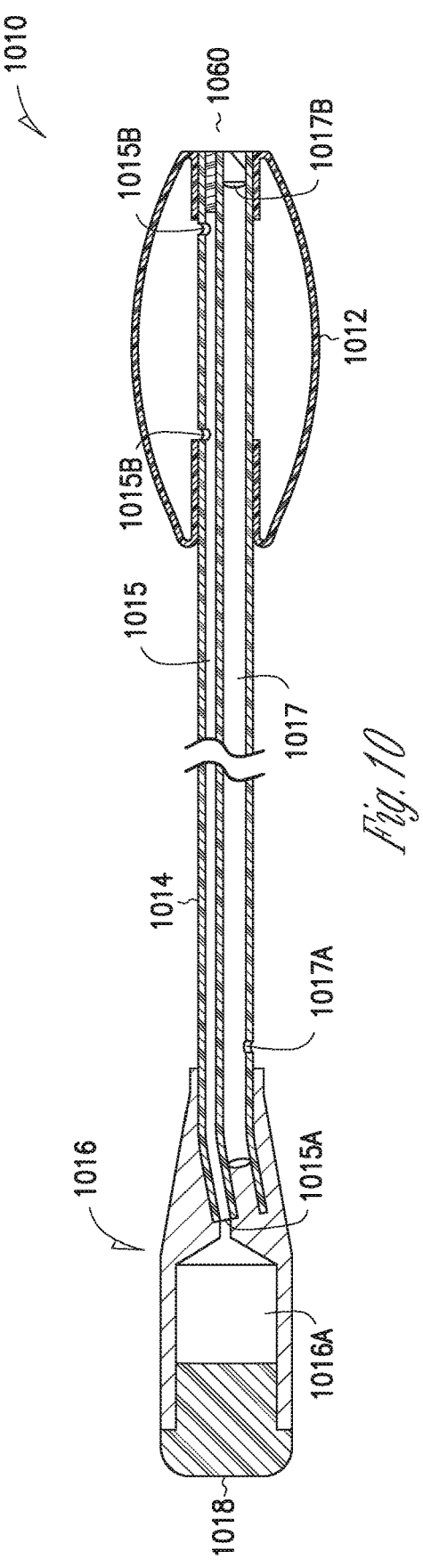

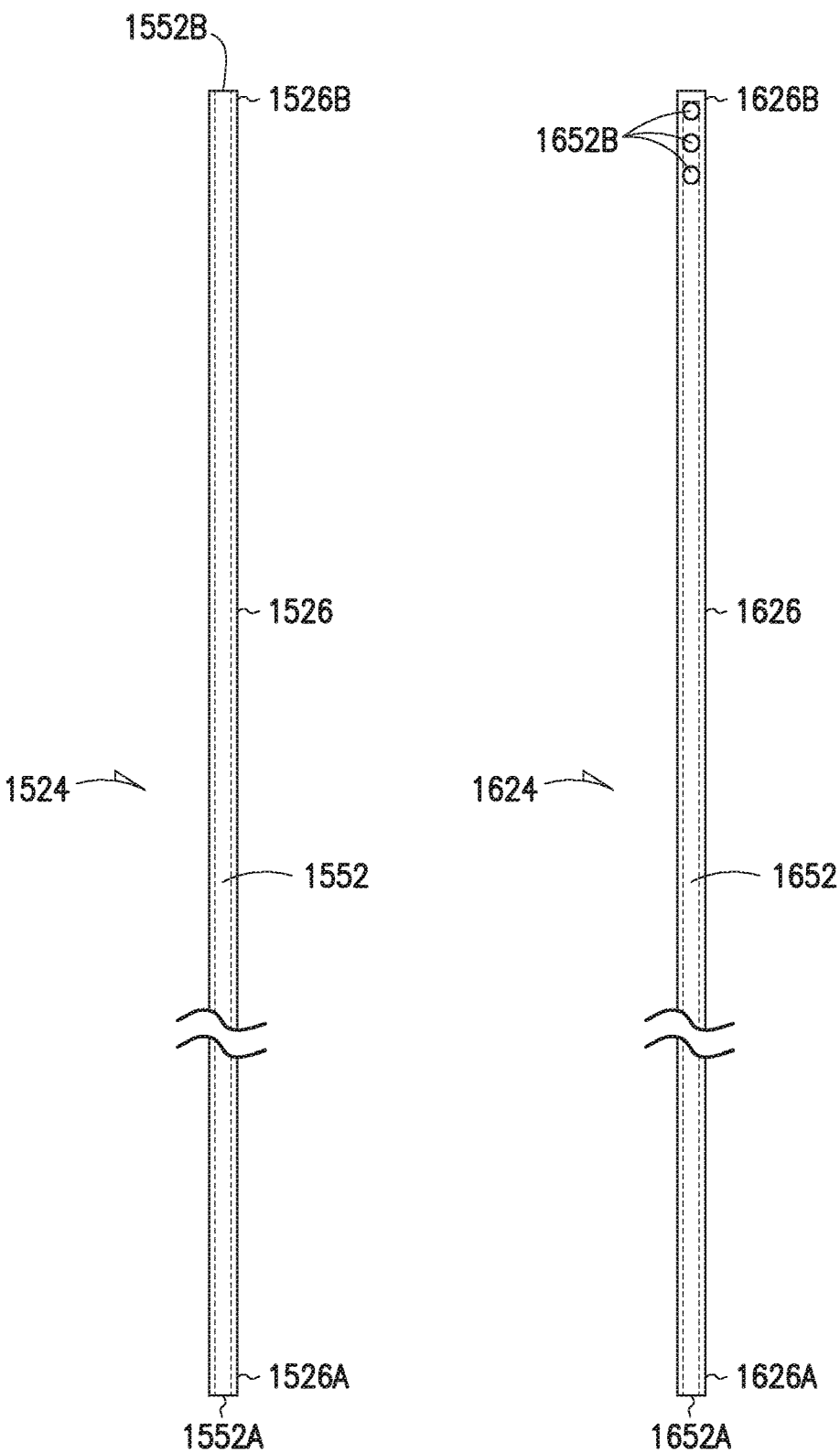

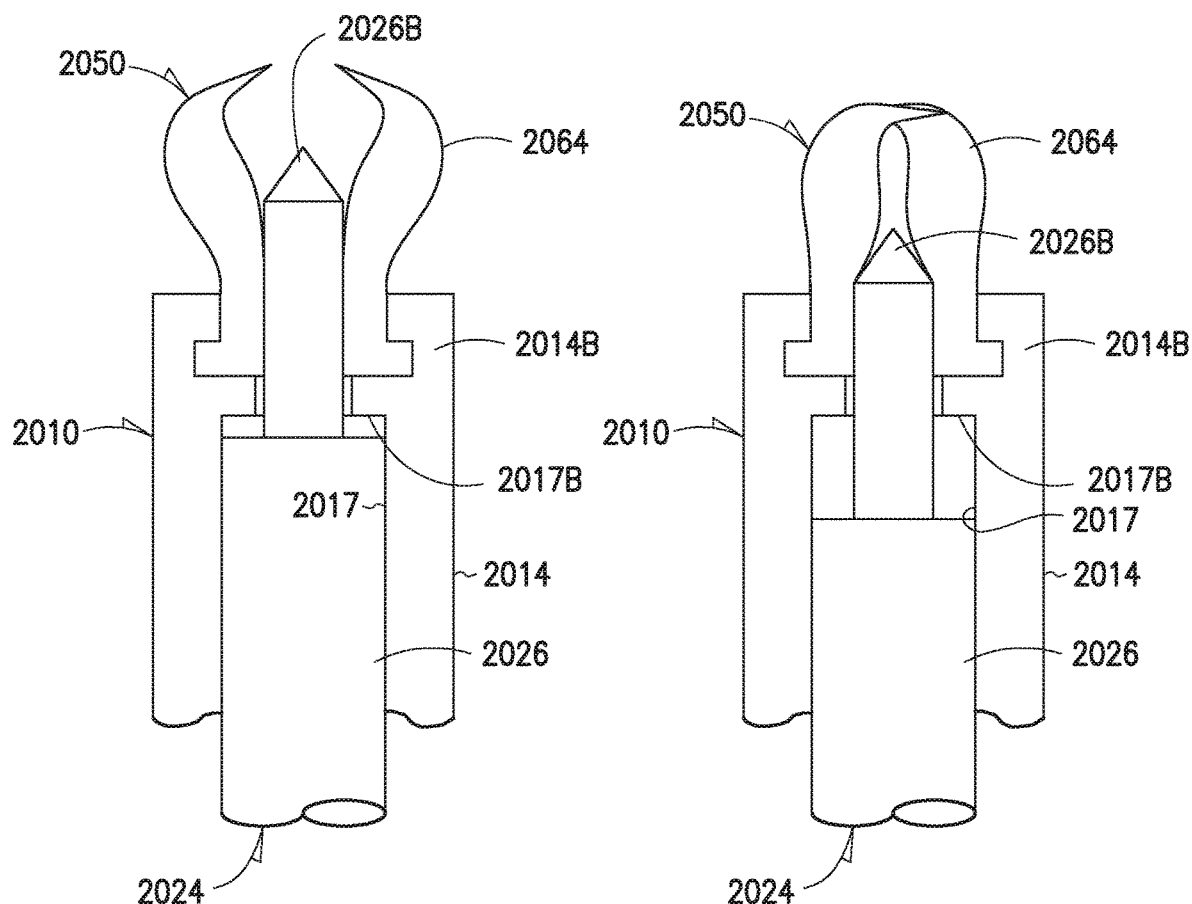
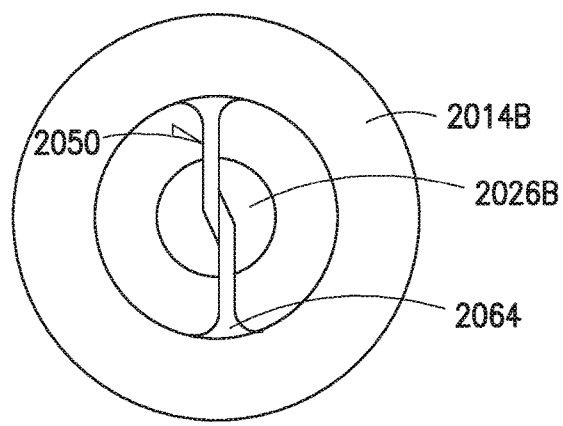

METHOD AND APPARATUS FOR FIXATION OF IMPLANTABLE DEVICE FOR URINARY CONTINENCE

CLAIM OF PRIORITY

This application is a continuation of U.S. patent application Ser. No. 16/949,991, filed Nov. 23, 2020, which claims the benefit of priority under 35 U.S.C. § 119(e) of U.S. Provisional Patent Application Ser. No. 63/042,947, entitled "METHOD AND APPARATUS FOR FIXATION OF IMPLANTABLE DEVICE FOR URINARY CONTINENCE", filed on Jun. 23, 2020, each of which are herein incorporated by reference in their entirety.

TECHNICAL FIELD

This document relates generally to implantable medical devices and more particularly to a method and apparatus for limiting migration of a device for treating urinary incontinence after its implantation in a patient.

BACKGROUND

An example of an implantable device for treating urinary incontinence includes an adjustable membrane element, such as a balloon, connected to a rear port with a conduit. The implantable device can be implanted in a patient with the adjustable membrane element placed adjacent to the patient's urethra and the rear port placed underneath the patient's skin by minimally invasive surgery. The adjustable membrane element can be adjusted during and after the surgery by injecting fluid into the rear port or extracting fluid from the rear port percutaneously using a needle. In an exemplary treatment, two of such implantable devices are placed in the patient such that the two adjustable membrane elements provide pressure and support at the patient's bladder neck to protect against accidental leaking of urine in cases such as stress urinary incontinence (e.g., leaking during sneeze, cough, or physical activity) or neurogenic bladder (e.g., leaking caused by spinal injury). The efficacy of this treatment depends on accurate placement of the adjustable membrane element at a target position in the patient, adjustment of the adjustable membrane element after the placement, and maintaining the position of the adjustable membrane element over time.

SUMMARY

An implantable device includes a conduit, an adjustable membrane element coupled to the conduit near the front end of the conduit for controllable coaptation of a body lumen, such as coaptation of a urethra as treatment for urinary incontinence, and a fixation mechanism at or near the front end of the conduit. In various embodiments, the fixation mechanism can anchor the implantable device to the tissue using a movement of a push wire. Optionally, the fixation mechanism can also allow the implantable device to be released from the tissue using another movement of the push wire, to allow for re-positioning or removal of the implantable device.

In one exemplary embodiment, an implantable device is configured to be positioned in tissue of a living body using a push wire for coaptation of a body lumen of the living body. The implantable device includes an adjustable membrane element, an elongate conduit, and a fixation mechanism. The adjustable membrane element includes a continuous wall having an inner surface defining a chamber. The elongate conduit includes a conduit peripheral surface, a conduit rear end, a conduit front end, and a push wire lumen. The conduit peripheral surface is connected to and sealed to the adjustable membrane element at or near the conduit front end. The push wire lumen extends longitudinally in the conduit and has an inlet to receive a portion of the push wire and a diameter suitable for accommodating the received portion of the push wire. The fixation mechanism is coupled to the conduit front end and configured to anchor the implantable device to the tissue using a movement of the push wire.

In another exemplary embodiment, a method for coapting a body lumen in tissue of a living body is provided. The method includes providing an implantable device and operating a fixation mechanism of the implantable device using a push wire. The implantable device includes an adjustable membrane element, an elongate conduit, and the fixation mechanism. The adjustable membrane element includes a continuous wall having an inner surface defining a chamber. The elongate conduit includes a conduit peripheral surface, a conduit rear end, a conduit front end, and a push wire lumen. The conduit peripheral surface is connected to and sealed to the adjustable membrane element at or near the conduit front end. The push wire lumen extends longitudinally in the conduit and has an inlet to receive a portion of the push wire and a diameter suitable for accommodating the received portion of the push wire. The fixation mechanism is configured to anchor the implantable device to the tissue.

This summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

FIG. 2 is a longitudinal cross-sectional view of the implantable device shown in FIG. 1, according to an embodiment of the present subject matter.

FIG. 3 is a cross-sectional view taken along line 3-3 of FIG. 2, according to an embodiment of the present subject matter.

FIG. 6 shows the implanted device after being expanded at the desired location in the body tissue of the patient to displace body tissue toward the body lumen for causing adjustable restriction of the body lumen, according to an embodiment of the present subject matter.

FIG. 7 is a cross-sectional view taken along line 7-7 of FIG. 6, according to an embodiment of the present subject matter.

FIG. 8 shows the implantable device after being inserted with its rear port underneath the skin of a patient, according to an embodiment of the present subject matter.

FIG. 9 is a schematic of another implantable device, according to an embodiment of the present subject matter.

FIG. 10 is a schematic of another implantable device, according to an embodiment of the present subject matter.

FIG. 15 is an illustration of another push wire, according to an embodiment of present subject matter.

FIG. 16 is an illustration of yet another push wire, according to an embodiment of present subject matter.

FIGS. 20A-20C are illustrations of a front end portion of an implantable device used with a push wire, where the implantable device includes a fixation mechanism including pincers, with FIG. 20A being a cross-sectional side view showing the pincers open, FIG. 20B being a cross-sectional side view showing the pincers closed, and FIG. 20C being an end view showing the pincers closed, according to an embodiment of present subject matter.

DETAILED DESCRIPTION

Figure 1:
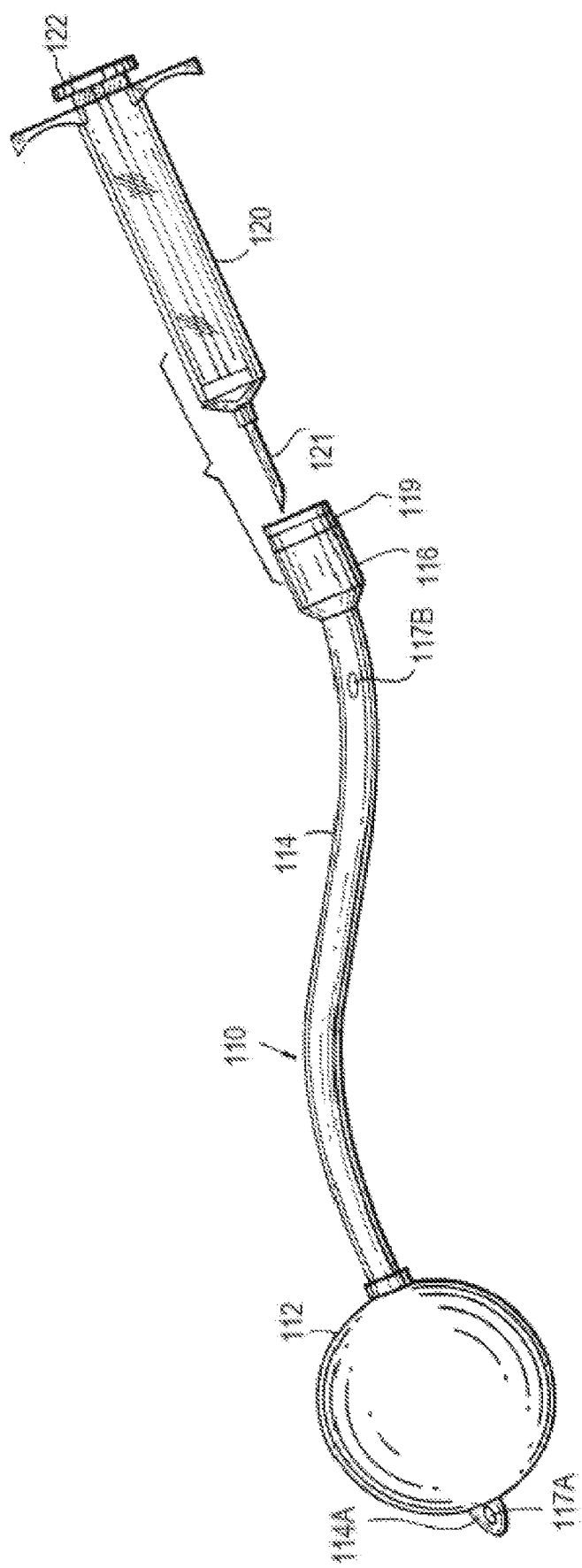
FIG. 1 is a perspective view of an implantable device and a syringe source for providing a flowable material to an adjustable membrane element of the implantable device, according to an embodiment of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

This document discusses, among other things, mechanisms for fixation of an implantable device to surrounding tissue for treating urinary incontinence. The implantable device can include, for example, an adjustable membrane element connected to a rear port with a conduit that has a lumen providing for fluid communication between a chamber of the adjustable membrane element and an interior cavity of the rear port. Various structural elements of the implantable device (e.g., the implantable device 110 shown in FIG. 1) discussed in this document may each be referred to by various terms. The "adjustable membrane element" (e.g., the adjustable membrane element 112 shown in FIG. 1) can also be referred to as, for example, an adjustable element, an expandable element, an expandable membrane element, a forward expandable membrane element, a balloon, or an adjustable balloon. The "conduit" (e.g., the conduit 114 shown in FIG. 1) can also be referred to as, for example, a central conduit element, a device conduit, a connecting conduit, a connecting conduit tube, or a tubular elongate body. The "rear port" (e.g., the rear port 116 shown in FIG. 1) can also be referred to as, for example, a rearward port portion or a rear port element. The "lumen" (e.g., the first lumen 215 and the second lumen 217 shown in FIG. 2) can also be referred to as, for example, a passageway, an inner passageway, or an interior passageway.

In an example, the implantable device includes an adjustable balloon connected to a port with a conduit. The balloon is placed adjacent the urethra to exert non-circumferential compression upon the urethral wall. The effectiveness of the therapy depends on proper positioning of the balloon in a patient's body, such as in the retropubic space near the urethra-vesical junction above the urogenital diaphragm in close proximity to the urethral walls. When two balloons (e.g., of two implantable devices) are used, their preferred positioning is usually symmetrical and lateral with respect to the urethra. Medical imaging techniques such as fluoroscopy or transrectal ultrasonography (TRUS) can be used to aid the positioning of the balloon(s). Sensors incorporated into the implantable device(s) and/or one or more surgical tools can also be used to aid the positioning of the balloon(s), such as discussed in U.S. patent application Ser. No. 16/450,246, filed on Jun. 24, 2019, assigned to UroMedica, Inc., which is incorporated by reference herein in its entirety.

During the implantation procedure, the implantable device(s) is(are) placed in the patient with the balloon(s) positioned and fixed in place at the target site(s). The balloon(s) is(are) only slightly inflated, typically up to 1.0 cc, for a period of 4 to 6 weeks to allow tissue encapsulation in order to stabilize the balloon(s) at its(their) target site(s). In particular, without encapsulation the implantable device(s) is(are) prone to migrate down the dilation path through which the implantable device(s) was(were) implanted. Thus, it is very important that fixation occur during this implantation procedure. After the encapsulation, the patient will go through one or more adjustment procedures during which the volume of fluid in the balloon(s) is adjusted to obtain and maintain urinary continence without causing undesirable obstruction.

The present subject matter provides an implantable device for treating urinary incontinence that has a fixation mechanism for preventing a balloon of the implantable device from unwanted displacement. FIGS. 1-10 illustrate various embodiments of an implantable device into which the fixation mechanism can be incorporated and a surgical tool used in the implantation that can also be used to activate and deactivate the fixation mechanism. The various embodiments of the implantable device and the surgical tool are illustrated in FIGS. 1-10 and discussed below by way of example, and not by way of restriction. These examples as well as additional examples of the implantable device and the surgical tool are discussed in U.S. Pat. Nos. 5,964,806, 6,045,498, 6,419,624, 6,579,224, and 8,926,494, all assigned to UroMedica, Inc., which are incorporated by reference herein in their entireties. FIGS. 13-24 illustrate various embodiments of the fixation mechanism incorporated onto the implantable device.

According to the present subject matter as shown by FIG. 1, there is provided an elongate implantable device 110, which includes an adjustable membrane element 112 shown in its full expanded size, and is attached pressure-tightly to an elongate conduit 114, which is connected to a rear port 116 communicating with the expandable element 112 through a first lumen 215 (see FIG. 2). The conduit 114 has a forward end 114A which extends slightly beyond the expandable element 112. A syringe 120 including a hollow needle 121 and a rear axially-movable plunger 122 is provided for adjustably injecting a suitable flowable material into the implantable device 110 through the rear port 116 to expand the adjustable membrane element 112.

In various embodiments, implantable medical device 110 can be positioned during the implantation procedure using a push wire (also referred to as a push rod) as a surgical tool. The conduit 114 contains one or two elongate lumens or passageways. Examples of implantable medical device 110 (without fixation mechanism) that are positioned using a push wire are illustrated in FIGS. 9 and 10.

In various other embodiments, implantable medical device 110 can be positioned during the implantation procedure using a guide probe (also referred to as a guide wire) as a surgical tool. The implantable procedure is known as an over-the-wire procedure. As further shown in FIGS. 2 and 3, the conduit 114 contains two elongate lumens or passageways. The first lumen 215 provides an internal passage by which the flowable material is directed from a cavity 216A in the rear port 116 to expand the adjustable membrane element 112. The conduit 114 is attached integrally to the rear port 116 at its rearward end. A second lumen 217 extends from a front opening 117A to a rearward opening 117B and serves to receive an elongate guide probe (shown in FIG. 4) and effect delivery of the implantable device 110 to a desired location in the body tissue of a patient.

An important feature of the implantable device 110 having the first lumen 215 includes a first opening 215A located in cavity 216A of the rear port 116 between an elastic septum 218 and the conduit 114 and is connected to the first lumen 215, so that a flowable material can be infused therethrough, and a second opening 215B serves to direct the working fluid to the adjustable membrane element 112. During adjustment of the volume of the membrane fluid provided from a hollow needle 121 of syringe 120, is infused through the septum 218 and continues through the conduit 114 connected to the adjustable membrane element 112. The rear port 116 preferably has a diameter greater than conduit 114 to accommodate the cavity 216A and the septum 218, which is retained securely by a clamp ring 119.

The entire implantable device 110 including the adjustable membrane element 112 is formed of a biocompatible material such as silicone or polyurethane elastomer, and the conduit 114 and the rear port 116 may be formed as a unitary construction. Optionally, the adjustable membrane element 112, the rear port 116, and the conduit 114 can be molded as one piece. As shown in FIG. 2, the adjustable membrane element 112 is adhered at 213 to conduit tube 114 at its forward end by a suitable adhesive material.

Figure 4:
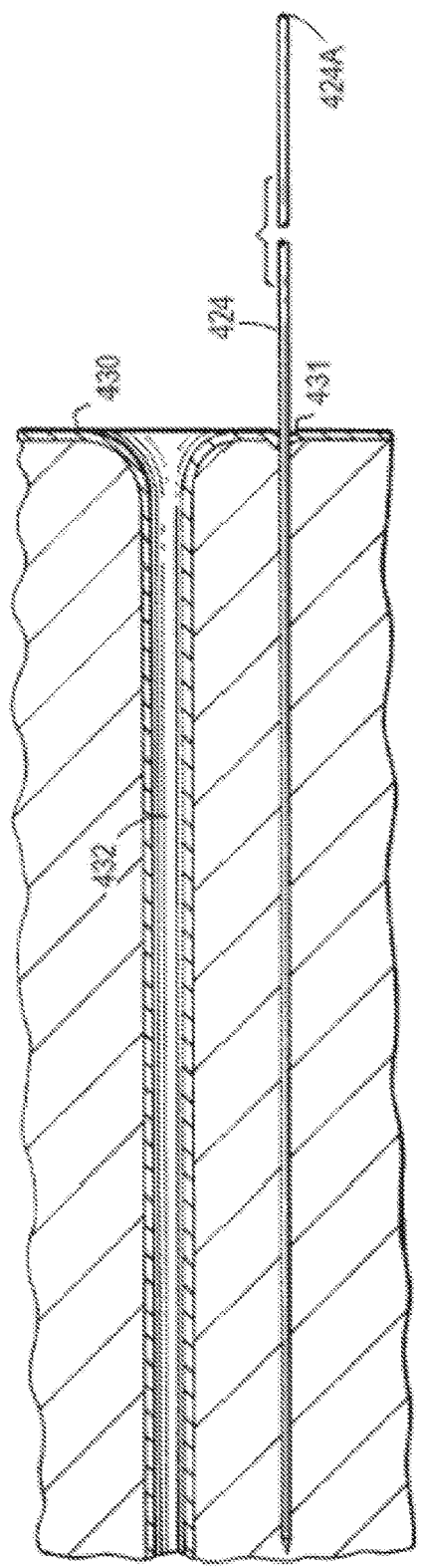
FIG. 4 illustrates a guide probe inserted into body tissue to an implant location adjacent a body lumen of a patient prior to insertion of the implantable device, according to an embodiment of the present subject matter.
Figure 5:
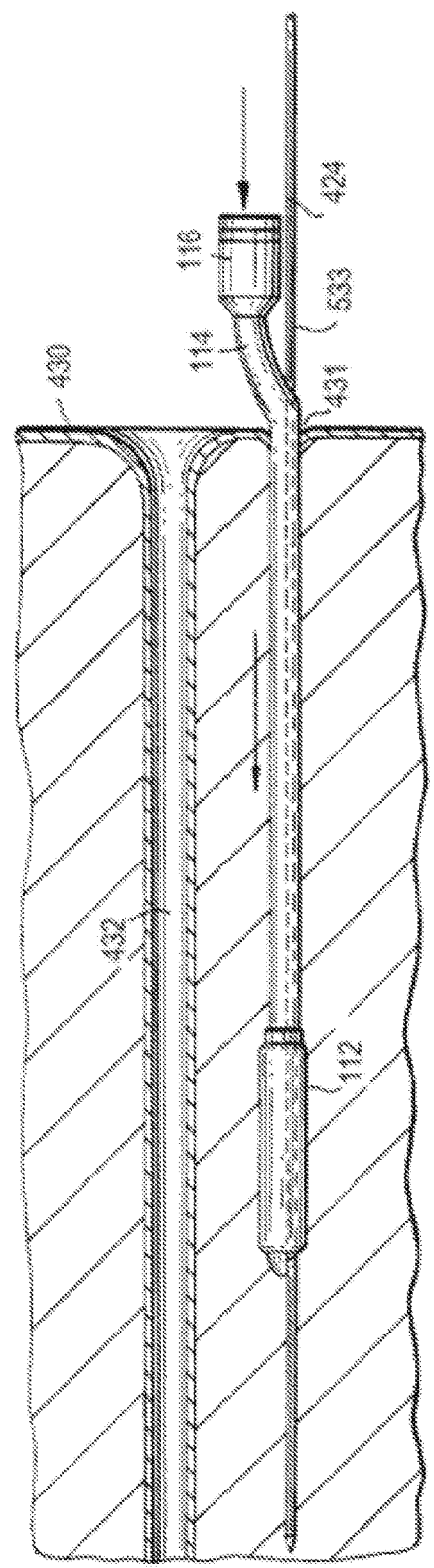
FIG. 5 shows the implantable device placed over the guide probe and partially advanced to the desired location with the adjustable membrane element being deflated, according to an embodiment of the present subject matter.

The implantable device and assembly according to the present subject matter can include three main members. The first member provided is an elongate guide in the form of a stiff solid elongate guide probe 424 (see FIG. 4) configured for delivery of the implantable device 110 to the desired site in the body tissue of a patient as generally shown by FIGS. 4 and 5. Alternatively, the elongate guide member can be in the form of a flexible guidewire which has been initially delivered into the body tissue through a separate hollow stiff probe that has been inserted to the desired location in the body tissue. The second member of the assembly is the implantable device 110 which includes the adjustable membrane element 112, the conduit 114 containing the two lumens 215 and 217, and the rear port 116. During its implantation, the implantable device 110 is guided to a pre-determined location adjacent a body lumen in a patient's body after the elongate solid guide probe 424 is first surgically inserted into the body tissue of the patient to establish an initial pathway. The lumen forward end opening 117A of the implantable device 110 is then disposed over the rear end of the guide probe 424 to guide the implantable device 110 and deliver the adjustable membrane element 112 (in its contracted shape) to the pre-determined location in the body tissue adjacent to the lumen which is to be adjustably restricted. The diameter of the second lumen 217 is made slightly larger than that of the guide probe 424 to permit the implantable device 110 to slide easily over the probe member.

During the implantation of the implantable device 110, a physician can first make a small incision in the skin 430 of the patient near a body lumen 432 that needs to be restricted, and then by visualization means such as fluoroscopy or ultrasonic imaging, the solid guide probe 424 is directed to the desired location, depending upon the anatomy of the patient. Thereafter, the opening 117A of the second lumen 117 of the conduit 114 with the adjustable membrane element 112 in its initial deflated or contracted condition, is slid over the rear end 424A of the guide probe 424. The forward end 114A of the conduit 114 can be made pointed to ease the passage of the implantable device 110 through the tissue. The guide probe 424 slides through the second lumen 217 of the conduit 114 and exits at the rearward opening 117B. As illustrated in FIG. 2, the opening 117B is between the adjustable membrane element 112 and the rear port 116. However, it may be advantageous to locate the opening 117B close to the adjustable membrane element 112 or, alternatively, to have the second lumen 217 extend through the rear port 116.

If desired, a mark 533 can be provided on the guide probe 424 which when aligned with a feature on the implantable device 110 such as the rear port 116 can assure that the implantable device 110 is appropriately placed at the correct depth in the patient's body tissue 430. It may be necessary to provide the conduit 114 in multiple lengths to facilitate placement of the septum 218 near the patient's skin. Alternatively, an effective length of the conduit 114 can be made adjustable by it having a helical shape similar to that of a coiled spring.

After the implantable device 110 has been advanced over guide probe 424 so that the contracted adjustable membrane element 112 is in the desired position adjacent to the body lumen 432, the body lumen 432 may be restricted to a desired degree by piercing septum 218 with the needle 121 of syringe 120 and injecting a flowable material through the first lumen 215 into the adjustable membrane element 112. The physician can determine the desired degree of restriction of body lumen 432 by means such as infusing fluid through the body lumen past the restriction and measuring the back pressure.

As illustrated by FIGS. 1 and 6, the source of flowable material is usually a syringe 120 with a hollow needle used to pierce the elastic septum 218. However, alternate fluid containers with means for making a reversible connection to the implantable device 110 could be used. The flowable material may be, for example, a saline solution, a flowable gel, or a slurry of particles in a liquid carrier. It may be advantageous to make the flowable material radiopaque so that the degree of membrane inflation may be viewed by x-ray.

An alternative method of delivery of the implantable device 110 can be to first withdraw the guide probe 424 from the body tissue and then inflate the adjustable membrane element 112. A further alternative would be to first place the implantable device 110 over the solid guide probe 424 outside the body and then insert them both into the body tissue as a unit. To facilitate this latter procedure, it may be desirable that there be some friction between the solid guide probe 424 and the second lumen 217 in the conduit 114.

After the implantable device 110 has been properly positioned with the adjustable membrane element 112 located near the body lumen 432 and the septum 218 in the rear port 116 located near the skin 430, the device is injected with a flowable material from the syringe 120. The expandable member can be inflated to a certain extent and then deflated to an extent suitable for encapsulation of the expandable member by body tissue. The guide probe 24 is then withdrawn from the device, leaving the slightly expanded membrane element in the body tissue. Then the skin incision 431 is closed over the port 116 by means such as a suture 834 as shown in FIG. 8.

The present subject matter provides the implantable device 110 with adjustability of the membrane expansion post-operatively. This adjustability is effected because the septum 218 is located remote from the adjustable membrane element 112 but near and under the patient's skin. The port and septum are located by, for instance, manual palpation of the skin region and the needle of the syringe is inserted through the skin and septum to add or remove material from the expandable member, thus increasing or decreasing the restriction of the body lumen.

To assure proper sealing of the septum 218, it is placed in compression within a cavity 216A by providing a tight metal ring 119 that surrounds the rear port 116 and is smaller in diameter than the port. When the needle 121 of the syringe 120 is withdrawn from the septum 218 after expansion or adjustment of the adjustable membrane element 112, there is positive sealing around the perimeter of the septum 218.

FIGS. 4-8 generally illustrate the "over-the-wire" method or procedure for properly implanting the implantable device 110 into the body tissue of a patient. As shown by FIG. 4, a physician, after locating the body lumen such as a urethra of the patient, makes a small incision 431 and inserts the guide probe 424 in the body tissue to a desired location adjacent the body lumen 432. This procedure is usually carried out under a local anesthetic with visual guidance, for instance under fluoroscopy, by the physician. Next, the physician takes the implantable device 110 and places it over the guide probe 424 through the second lumen 217 as shown in FIGS. 1 and 2. The guide probe 424 enters the rear opening 117B and exits the forward opening 117A. The implantable device 110, with the conduit 114 being sufficiently flexible, is advanced along the guide probe 424 into the body tissue.

After the desired location within the body tissue has been reached, a suitable flowable material is introduced into the implantable device 110 from a source such as the syringe 120 having hollow needle 121 inserted through septum 218 to at least partially expand the adjustable membrane element 112, as shown by FIG. 6. Next, the guide probe 424 is removed and the adjustable membrane element 112 is expanded further to the desired enlarged size for restriction of the body lumen 432. The syringe 120 is removed from the implantable device 110, after which the desired size of the adjustable membrane element 112 is maintained by the elastic septum 218. Next, the patient's incision at 431 is surgically closed over the port 116 and septum 218 by sutures at 834.

FIGS. 9-24 illustrate examples of an implantable device that can be positioned using a push wire and examples of the push wire. The method or procedure for properly implanting such an implantable device into the body tissue of a patient is similar to the over-the-wire method or procedure as illustrated in FIGS. 4-8, except for using a push wire instead of the guide probe. After locating the body lumen such as a urethra of the patient, the physician makes an incision and inserts a sheath in the body tissue to a desired location adjacent the body lumen. Next, the physician places the implantable device, which can be provided pre-assembled with the push wire inserted into its push wire lumen, in the sheath and pushes the push wire to advance the implantable device into the body tissue until the desired location within the body tissue has been reached. Then, the sheath is removed from the tissue of the patient, and the adjustable membrane element of the implantable device is expanded to the desired size.

FIG. 9 is an illustration of an implantable device kit 940, showing a cross-sectional view, according to one embodiment of the present subject matter. The implantable device kit 940 includes an implantable device 910 having an adjustable membrane element 912 and an elongate conduit 914, where the conduit 914 includes at least a first lumen 915 which extends longitudinally in the conduit 914 from a first opening 915A at a rear end (also referred to as a proximal end) 962 to a second opening 915B, and where the implantable device 910 is shown positioned within a channel 944 of a sheath 946.

The implantable device kit 940 further includes a rear port 916, where the rear port 916 is coupled to the rear end 962 of the conduit 914. In one embodiment, the rear port 916 is coupled to the rear end 962 of the elongate body 914 using chemical adhesives, or alternatively, using sonic welding techniques as are known in the art. In an additional embodiment, the rear port 916 and rear end 962 are formed together in a polymer molding process, such as liquid injection molding, as are known in the art.

The rear port 916 includes a cavity 916A, where the cavity 916A is in fluid communication with the first opening 915A of the conduit 914. In one embodiment, the rear port 916 also includes an elastic septum 918 through which the cavity 916A is accessed, where the elastic septum 918 is self-sealing after repeated pierces, for example, with a needle. In one embodiment, the elastic septum 918 is retained in the rear port 916 by a clamp ring 919 located around the rear port 916. In one embodiment, the clamp ring 919 is made of a biocompatible material, such as, for example, titanium. In one embodiment, the elastic septum 918 is made of a biocompatible material, such as, for example, silicone or polyurethane. The rear port 916 has an outer diameter defined by an outer surface 954 of the rear port 916. In one embodiment, the rear port 916 has an outer diameter of 1 to 15 millimeters, with 4.5 millimeters being a specific example.

In one embodiment, the outer surface of the rear port 916 and the adjustable membrane element 912 are of a size (e.g., a diameter) that is smaller than an inner size (e.g., a diameter) of the channel 944 to allow the implantable device 910 to be moved longitudinally through the channel 944 of the sheath 946. In an alternative embodiment, the rear port 916 is constructed of at least one material flexible enough to allow the size of the rear port 916 in its relaxed state to be compressed to a size sufficiently small so that the implantable device 910 can be moved longitudinally through the channel 944 of the sheath 946. In various embodiments, the conduit 914 has a stiffness sufficient to allow force applied at the rear end of its tubular elongate body to move the implantable device 910 at least partially through the channel 944 of the sheath 946. In one embodiment, the stiffness of the conduit 914 is determined based on the type of material used in constructing its tubular elongate body. Alternatively, support elements can be added to the tubular elongate body. For example, a metal coil can be placed longitudinally within the tubular elongate body to increase the stiffness of the tubular elongate body.

Once the implantable device 910 is positioned within a body, the adjustable membrane element 912 is inflated by releasably connecting a flowable material source to the rear port 916. In one embodiment, the flowable material source includes a syringe with a non-coring needle, where the needle is inserted through the elastic septum 918. A measured supply of fluid volume can be introduced into the implantable device 910, and the adjustable membrane element 912 expands or contracts due to a volume of flowable material introduced into the cavity 916A of the rear port 916 from the flowable material source. The adjustable membrane element 912 is then used to at least partially and adjustably restrict the body lumen. Fluids suitable for infusing into the prosthesis include, but are not limited to, normal saline, polymer gels such as silicone gels or hydrogels of polyvinylpyrrolidone, polyethylene glycol, or carboxy methyl cellulose for example, high viscosity liquids such as hyaluronic acid, dextran, polyacrylic acid, polyvinyl alcohol, or a radio-opaque fluid such as isotonic contrast media for example. Once the adjustable membrane element 912 has been inflated, the needle is withdrawn from the septum of the rear port 916. In an additional embodiment, a detectable marker 970 is imbedded in the continuous wall of the adjustable membrane element 912. The detectable marker 970 allows the adjustable membrane element 912 to be located within the tissues of a patient using any number of visualization techniques which employ electromagnetic energy as a means of locating objects within the body. In one embodiment, the detectable marker 970 is constructed of tantalum and the visualization techniques used to visualize the adjustable membrane element 912 are x-ray or fluoroscopy as are known in the art.

In an additional embodiment, a detectable marker is imbedded in the implantable device 910. For example, the detectable marker 970 is located at a front end (also referred to as a distal end) 960 (e.g., the tip) of the conduit 914. Alternatively, the detectable marker can be located in the continuous wall of the adjustable membrane element 912. The detectable marker 970 allows the front end 960, or the adjustable membrane element 912, to be located within the tissues of a patient using any number of visualization techniques which employ electromagnetic energy as a means of locating objects within the body. In one embodiment, the detectable marker 970 is constructed of tantalum and the visualization techniques used to visualize the front end 960, or the adjustable membrane element 912, are x-ray or fluoroscopy as are known in the art. In an additional embodiment, the sheath could also have a detectable marker, where the marker could be incorporated into, or on, the wall of the sheath. Alternatively, the entire sheath could be constructed to be radio-opaque.

FIG. 10 is an illustration of an additional embodiment of an implantable device 1010 according to the present subject matter. The implantable device 1010 includes an adjustable membrane element 1012 and a conduit 1014. The conduit 1014 has a front end 1060. In one embodiment, the peripheral surface of the conduit 1014 is connected to and sealed to the adjustable membrane element 1012. In one embodiment, the adjustable membrane element 1012 includes a continuous wall having an inner surface defining a chamber.

The conduit 1014 includes a first lumen 1015 and a second lumen 1017. In one embodiment, the first lumen 1015 extends longitudinally in the conduit 1014 from a first opening 1015A to one or more second openings 1015B (e.g., two openings as shown in FIG. 10). The second opening(s) 1015B is(are) in fluid communication with the chamber of adjustable membrane element 1012 for adjustably expanding or contracting the adjustable membrane element 1012 by flowable material introduced through the first opening 1015A. To prevent leakage of the fluid from the adjustable membrane element 1012, the first lumen 1015 has a closed end at or near the front end 1060 of the conduit 1014. The closed end can be formed by sealing the front end of the first lumen 1015, for example, using silicone adhesive. Alternatively, the first lumen 1015 can be constructed by manufacturing to end before reaching the front end of the conduit 1014.

The second lumen 1017 extends longitudinally along the conduit 1014 from an inlet 1017A to a closed end 1017B at the front end 1060. In one embodiment, the second lumen 1017 and the inlet 1017A are each of sufficient diameter to receive a push rod that can be used to advance the implantable device 1010 in the tissue.

The implantable device 1010 further includes a rear port 1016, which is coupled to the rear end of the conduit 1014. In one embodiment, the rear port 1016 is similar to the rear port 916 and includes a cavity 1016A and an elastic septum 1018. The cavity 1016A coupled to and in fluid communication with the first lumen 1015 at the first opening 1015A. The elastic septum 1018 allows for access to the cavity 1016A using a needle for introducing and/or withdrawing fluid to expand (inflate) and/or contract (deflate) the adjustable membrane element 1012. The diameter of the elastic septum 1018 can be slightly larger than the diameter of the cavity 1016A to produce compression to the elastic septum 1018 for better sealing.

Figure 11:
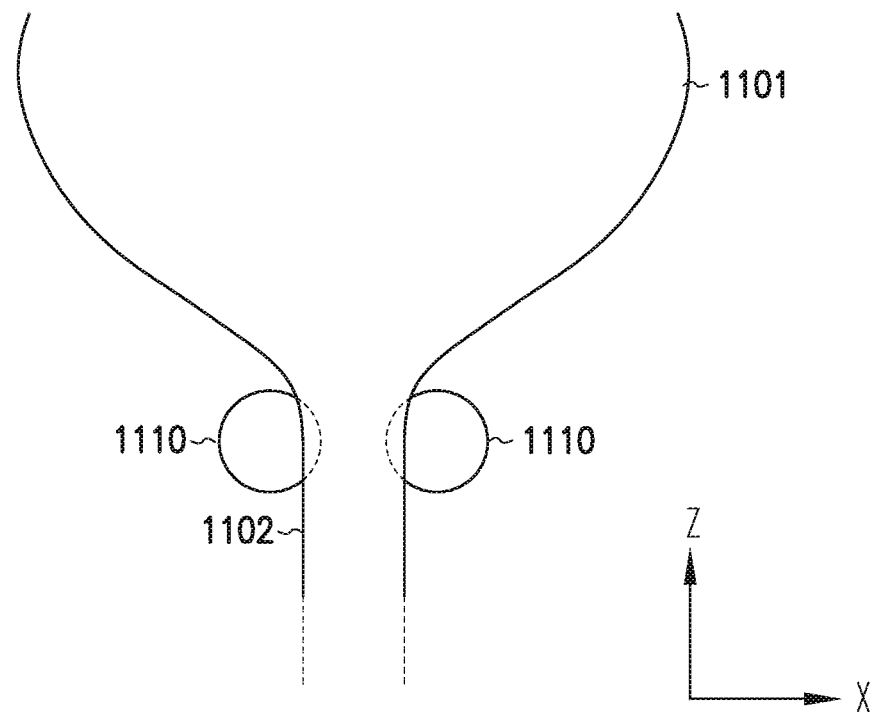
FIG. 11 is a top view showing approximate target sites of placement of implantable devices to improve coaptation of a urethra, according to an embodiment of present subject matter.

FIG. 11 is a top view of a bladder 1101 and a urethra 1102 showing approximate target sites of placement of the implantable devices 1110 to improve coaptation of the urethra, according to an embodiment of the present subject matter. The implantable devices 1110 can represent any embodiment of the implantable device as discussed in this document (with the expandable membrane element or the adjustable membrane element shown in the figure to illustrate its location), including but not limited to the implantable device 110, the implantable device 910, the implantable device 1010, or an implantable device including various combinations of features of the implantable devices 110, 910, and 1010. A Cartesian coordinate system with X-, Y-, and Z-axes is shown in FIGS. 11-14 (with two of the X-, Y-, and Z-axes seen in each of these figures) as a reference for exemplary orientations of structures illustrated in these figures. The orientation of the Z-axis is along the direction of the urethra 1002 in the approximate location of implantation. The location is near the bladder neck and urethral vesical anastomosis in the case of radical prostatectomy or further down the urethra at the apex of the prostate after trans-urethral resection of the prostate (TURP).

Figure 12:
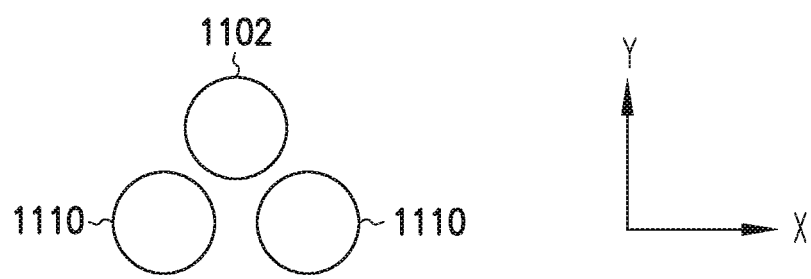
FIG. 12 is a view along the length of the urethra in the area of implantation showing approximate target sites of placement of implantable devices to improve coaptation of a urethra, according to an embodiment of present subject matter.

FIG. 12 is a view along the length of the urethra 1102 in the area of implantation (or along the Y-axis) showing approximate target sites of placement of the implantable devices 1110 to improve coaptation of a urethra, according to an embodiment of present subject matter. The present subject matter can assist in the proper placement of the implantable devices 1110 during implantation into the patient and/or adjustment of the implantable devices 1110 after the implantation. In particular, the accurate placement of the implantable devices 1110 along the Y-axis (sagittal view) is facilitated by the applications of the present subject matter.

Figure 13:
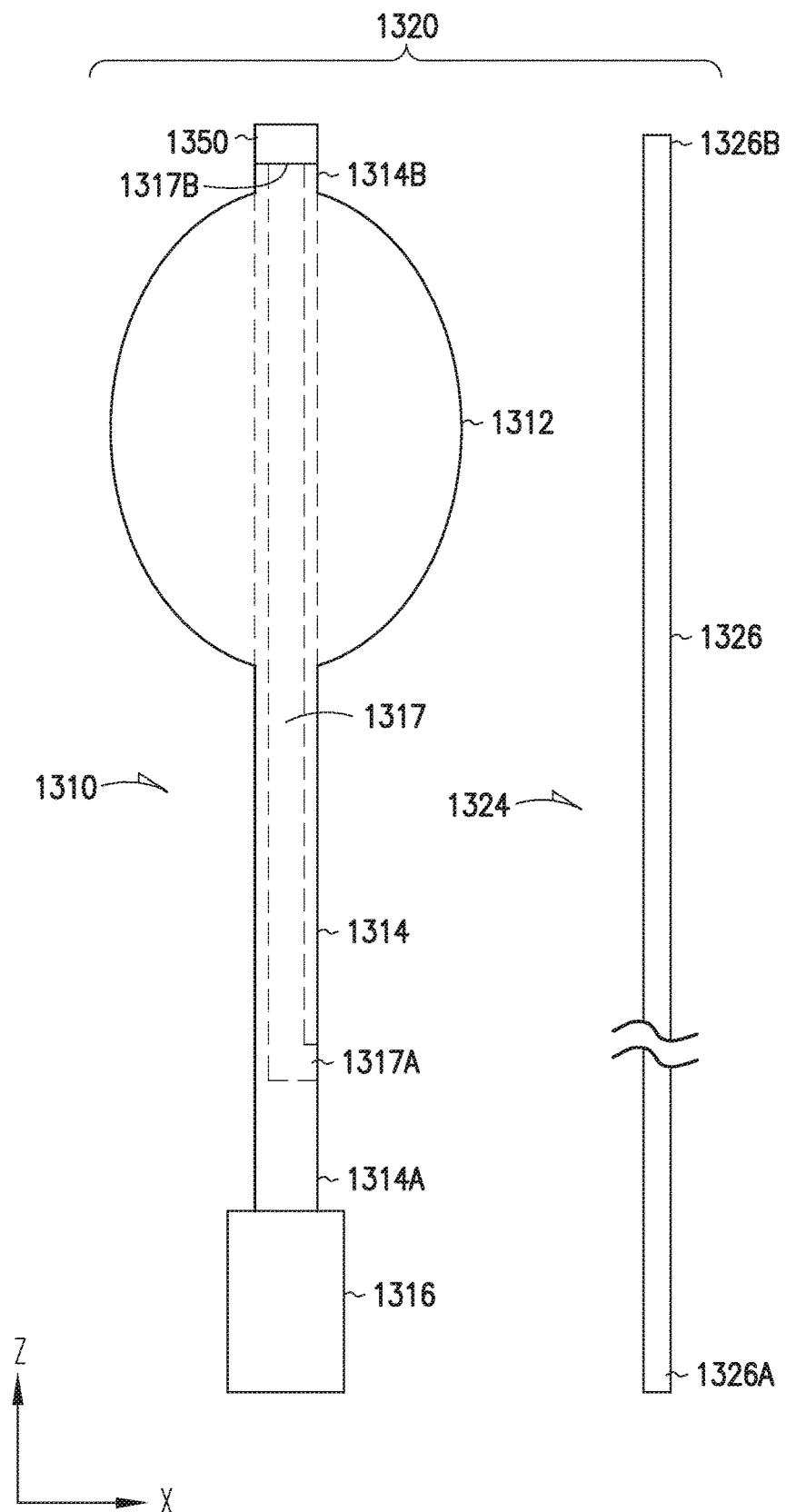
FIG. 13 is an illustration of an implantable device and a push wire, according to an embodiment of present subject matter.

FIG. 13 is an illustration of an implantable device kit 1320, including an implantable device 1310 and a push wire 1324, according to an embodiment of present subject matter. The implantable device 1310 and the push wire 1324 can be provided as a device kit, which may also include other accessories. The implantable device 1310 can be used to coapt a lumen in a body, and can include an adjustable membrane element 1312, an elongate the conduit 1314, a rear port 1316, and a fixation mechanism 1350. The adjustable membrane element 1312 is configured to coapt the lumen and includes a continuous wall having an inner surface defining a chamber. The conduit 1314 has a conduit rear end 1314A, a conduit front end 1314B coupled to the adjustable membrane element 1312, a peripheral surface connected to and sealed to the adjustable membrane element 1312 near the conduit front end 1314B, and a push wire lumen 1317 extending longitudinally in the conduit 1314 from a lumen inlet 1317A near the conduit rear end 1314A to a lumen front end 1317B at the conduit front end 1314B. The lumen inlet 1317A has a size allowing a portion of the push wire 1324 to enter. The lumen front end 1317B can be a closed front end allowing the push wire 1324 to push the implantable device 1310 or an outlet to allow a portion of the push wire 1324 to exit, depending on the type of the fixation mechanism 1350. The push wire lumen 1317 has a diameter to accommodate at least the portion of the push wire 1324 that enters through the lumen inlet 1317A. The diameter is suitable for the push wire 1324 to move longitudinally in the push wire lumen 1317 by pushing a portion of the push wire 1324 that is outside of the conduit 1314. Longitudinal movements of the push wire 1324 can be used to operate the fixation mechanism 1350, in addition to advance the implantable device 1310 in the tissue. The diameter can also be suitable for the push wire 1324 to rotate in the push wire lumen 1317 by rotating a portion of the push wire 1324 that is outside of the conduit 1314, when rotational movements of the push wire 1324 are used to operate the fixation mechanism 1350.

The rear port 1316 is coupled to the conduit read end 1314A, and includes a cavity in fluid communication with the chamber of the adjustable membrane element 1312 though an inflation lumen in the conduit 1314 (not shown in FIG. 13) to allow for expansion of the adjustable membrane element 1312 by injecting a fluid into the chamber and contraction of the adjustable membrane element 1312 by withdrawing the fluid from the chamber. In some embodiments, the rear port 1316 is releasably coupled to the conduit rear end 1314A.

In various embodiments, implantable device 1310 is a multi-lumen (e.g., dual lumen) implantable device including the push wire lumen 1317 and the inflation lumen (not shown in FIG. 13) as separate lumens.

The fixation mechanism 1350 is coupled to the conduit front end 1314B to limit displacement of the implantable device 1310 in the tissue after implantation by anchoring the implantable device 1310 to the tissue. In various embodiments, the fixation mechanism 1350 can anchor the implantable device 1310 to the tissue by actively trapping a portion of the tissue in the fixation mechanism 1350. The fixation mechanism 1350 includes sufficient space to maintain viability of the trapped portion of the tissue on a permanent basis. The fixation mechanism 1350 can also allow the trapped portion of the tissue to be released for repositioning of the implantable device 1310 in the tissue or removal of the implantable device 1310 from the tissue. In various other embodiments, the fixation mechanism 1350 can anchor the implantable device 1310 to the tissue by extending an anchoring member into the tissue. The fixation mechanism 1350 can also allow the anchoring member to be detached from the tissue for repositioning of the implantable device 1310 in the tissue or removal of the implantable device 1310 from the tissue.

The implantable devices 1310 can present a combination of the fixation mechanism 1350 with a suitable implantable device selected from those discussed with reference to FIGS. 1-10, including but not limited to the implantable device 110, the implantable device 1010, or an implantable device including various combinations of features of the implantable devices 110, 910, and 1010.

The push wire 1324 has an elongate push wire body 1326 having a push wire rear end 1326A and a push wire front end 1326B. The push wire front end 1326B can have any shape suitable for advancing the implantable device 1310 in the tissue as well as operating (e.g., activating and/or deactivating) the fixation mechanism 1350. The elongate push wire body 1326 has a diameter suitable for moving longitudinally in the push wire lumen 1317 of the conduit 1314. The longitudinal movements of the push wire 1324 includes moving the push wire 1324 along its own longitudinal axis (which is also substantially parallel to the longitudinal axis of the conduit 1314). The diameter can also be suitable for rotating in the push wire lumen 1317 of the conduit 1314. The rotational movements of the push wire 1324 includes rotating the push wire 1324 about its own longitudinal axis.

In this document, "activation" of a fixation mechanism refers to the operation of the fixation mechanism that anchors an implantable device to tissue, and "deactivation" of the fixation mechanism refers to the operation that releases the implantable device from the tissue. Thus, the fixation mechanism is active (i.e., in its activated state) when it is in a state intended for anchoring the implantable device to the tissue, and is inactive (i.e., in its deactivated state) when it is in a state not intended for anchoring the implantable device to the tissue.

In this document, terms including "substantial", "substantially", "approximate", "approximately", or the like can refer to imperfection or inaccuracy resulting from practical factors including, but not limited to, accuracy in manual handling and errors within manufacturing tolerances. For example, the longitudinal axes of the push wire and the push wire lumen of the conduit can be "substantially parallel" when the former is partially placed in the latter because they are not perfectly parallel due to (1) errors within their manufacturing tolerances, (2) manually controlled movements of the push wire in the push wire lumen, and (3) a portion of the push wire is not in the push wire lumen, among other things. Such terms ("substantial", "substantially", "approximate", "approximately", or the like" can also refer to small deviations by design. For example, a push wire lumen can be "substantially parallel" to the longitudinal axes of the conduit while a small portion of the push wire lumen next to the inlet (on a lateral side of the conduit) deviates from being parallel to the longitudinal axes of the conduit by design. In a multi-lumen implantable device, the push wire lumen can be "substantially parallel" to the longitudinal axes of the conduit. While a major portion of this push wire lumen can be off-center in the conduit to allow space for inflation lumen, the front-end portion of the push wire lumen can deviate from being parallel to the longitudinal axes of the conduit to end at the center of the front end of the conduit.

Figure 14:
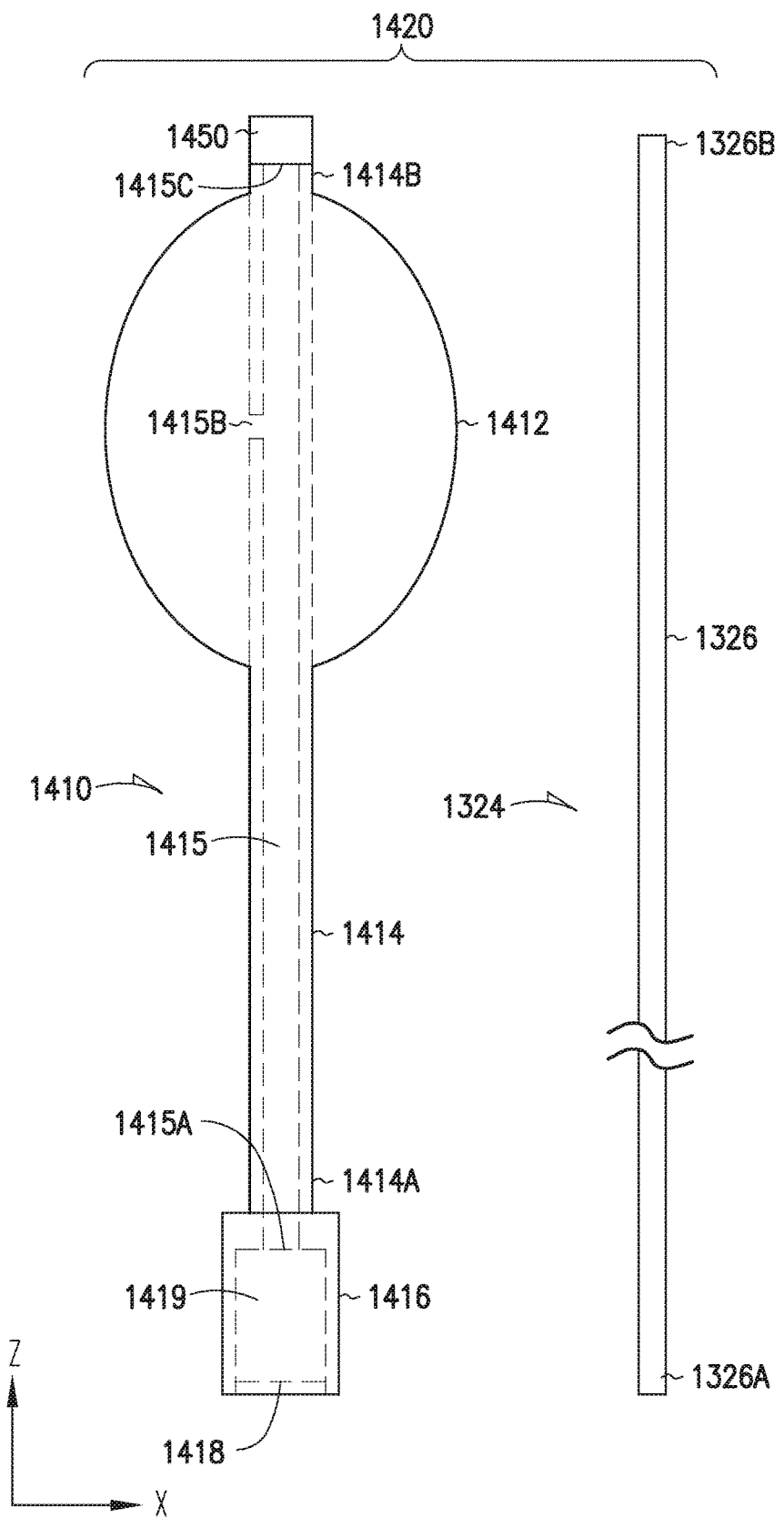
FIG. 14 is an illustration of another implantable device and the push wire, according to an embodiment of present subject matter.

FIG. 14 is an illustration of an implantable device kit 1420, including an implantable device 1410 and the push wire 1324, according to an embodiment of present subject matter. The implantable device 1410 and the push wire 1324 can be provided as a device kit, which may also include other accessories. The implantable device 1410 can be used to coapt a lumen in a body, and can include an adjustable membrane element 1412, an elongate the conduit 1414, a rear port 1416, and a fixation mechanism 1450. The adjustable membrane element 1412 is configured to coapt the lumen and includes a continuous wall having an inner surface defining a chamber. The conduit 1414 has a conduit rear end 1414A, a conduit front end 1414B coupled to the adjustable membrane element 1412, a peripheral surface connected to and sealed to the adjustable membrane element 1412 near the conduit front end 1414B, and an inflation lumen 1415 extending longitudinally in the conduit 1414. The inflation lumen 1415 has a lumen rear opening 1415A at the conduit rear end 1414A, a lumen front opening 1415B in fluid communication with the chamber of the adjustable membrane element 1412 to allow for expansion of the adjustable membrane element 1412 by injecting a fluid into the chamber and contraction of the adjustable membrane element 1412 by withdrawing the fluid from the chamber, and a lumen front end 1415C to allow the push wire 1324 to advance the implantable device 1410 in the tissue and/or to operate fixation mechanism 1450. Lumen front end 1415C is a closed end that does not allow the fluid to leak out of the lumen 1415.

The rear port 1416 is coupled to the conduit rear end 1414A, and includes a cavity 1419 in fluid communication with the chamber of the adjustable membrane element 1412 though the inflation lumen 1415 to allow for expansion of the adjustable membrane element 1412 by injecting a fluid into the chamber and contraction of the adjustable membrane element 1412 by withdrawing the fluid from the chamber. The cavity 1419 is sealed by a septum 1418 that is elastic and self-sealing after being pierced through, for example by a hollow needle coupled to a syringe for injecting and withdrawing the fluid. In some embodiments, the rear port 1416 is releasably coupled to the conduit rear end 1414A.

In various embodiments, the implantable device 1410 is a single-lumen implantable device with the inflation lumen 1415 also functioning as a push wire lumen. The inflation lumen 1415 meets the requirements for the push wire lumen 1317 as discussed above, with the push wire lumen inlet being the inflation lumen rear end 1415A. The push wire 1324 enters inflation lumen 1415 by piercing through the septum 1418.

The fixation mechanism 1450 is coupled to the conduit front end 1414B to limit displacement of the implantable device 1410 in the tissue after implantation by anchoring the implantable device 1410 to the tissue. In various embodiments, the fixation mechanism 1450 can anchor the implantable device 1410 to the tissue by actively trapping a portion of the tissue in the fixation device 1450. The fixation mechanism 1450 includes sufficient space to maintain viability of the trapped portion of the tissue on a permanent basis. The fixation mechanism 1450 can also allow the trapped portion of the tissue to be released for repositioning of the implantable device 1410 in the tissue or removal of the implantable device 1410 from the tissue. In various other embodiments, the fixation mechanism 1450 can anchor the implantable device 1410 to the tissue by extending an anchoring member into the tissue. The fixation mechanism 1450 can also allow for retraction of the anchoring member from the tissue for repositioning of the implantable device 1410 in the tissue or removal of the implantable device 1410 from the tissue. In various embodiments, the fixation mechanism 1450 functions with the lumen 1415 that is leak-proof at the lumen front end 1415C (while the fixation mechanism 1350 may or may not require the push wire 1324 to exit from the lumen frond end 1317B to operate).

The implantable devices 1410 can present a combination of the fixation mechanism 1450 with a suitable implantable device selected from those discussed with reference to FIGS. 1-10, including but not limited to the implantable device 910 or an implantable device including various combinations of features of the implantable devices 110, 910, and 1010.

FIG. 15 is an illustration of another push wire 1524, according to an embodiment of present subject matter. The implantable device kit 1320 or 1420 can include the push wire 1524, in addition to or in place of push wire 1324. The push wire 1524 is a hollow-core push wire that includes an elongate push wire body 1526 and a core lumen 1552 extending longitudinally in the push wire body 1526. The push wire body 1526 having a push wire rear end 1526A and a push wire front end 1526B. The core lumen 1552 has a rear opening 1552A at the push wire rear end 1526A and a front opening 1552B at the push wire front end 1526B. In addition to the functions of the push wire 1324, the push wire 1524 allows for a fluid to be injected into, and withdrawn from, an area in or about the fixation device 1350 or 1450.

FIG. 16 is an illustration of yet another push wire 1624, according to an embodiment of present subject matter. The implantable device kit 1320 or 1420 can include the push wire 1624, in addition to or in place of push wires 1324 and/or 1524. The push wire 1624 is another hollow-core push wire that includes an elongate push wire body 1626 and a core lumen 1652 extending longitudinally in the push wire body 1626. The push wire body 1626 having a push wire rear end 1626A and a push wire front end 1626B. The core lumen 1652 has a rear opening 1652A at the push wire rear end 1526A and multiple front openings 1652B at and/or near the push wire front end 1626B. In addition to the functions of the push wire 1324, the push wire 1624 allows for a fluid to be injected into, and withdrawn from, an area in or about the fixation device 1350 or 1450.

Fixation Mechanism Examples

Various examples for the fixation mechanisms 1350 and 1450 are discussed below. Each example may be suitable for use as one or both of the fixation mechanisms 1350 and 1450, as those skilled in the art will understand upon reading this document. For example, some examples may require a push wire lumen with an open lumen front end, thereby being suitable for use as part of implantable device 1310, while some other examples may allow for use with a push wire or inflation lumen with a closed (leak-proof) front lumen end, thereby being suitable for use as part of implantable device 1410. These examples are provided to illustrate, rather than restrict, various fixation mechanisms according to the present subject matter.

1. To Anchor/Release Via Push Wire

In various embodiments, a fixation mechanism (e.g., fixation mechanism 1350 or 1450) can anchor an implantable device (e.g., implantable device 1310 or 1410) to the tissue by receiving an energy transmitted using a push wire (e.g., the push wire 1324, 1524, or 1624). In various further embodiments, the fixation mechanism can also release the implantable device from the tissue by receiving another energy transmitted using the push wire.

1.1. Using Longitudinal Movements of Push Wire

In various embodiments, the fixation mechanism can anchor the implantable device to the tissue (i.e., be activated) by engaging a portion of the tissue using a longitudinal movement of the push wire in a forward direction and trapping the engaged portion of the tissue using a longitudinal movement of the push wire in a reverse direction. The longitudinal movement of the push wire in the forward direction results from pushing the push wire, i.e., applying a force toward the conduit front end. The longitudinal movement of the push wire in the reverse direction can result from pulling the push wire and/or stopping the pushing, depending the type of the fixation mechanism. In various further embodiments, the fixation mechanism can also release the implantable device from the tissue (i.e., be deactivated) by expelling the trapped portion of the tissue using additional longitudinal movements of the push wire without re-trapping another portion of the tissue. In some embodiments, the fixation mechanism can be kept in a deactivated state after the implantable device is released from the tissue to prevent it from unintentionally engaging and trapping another portion of the tissue while the implantable device is still in the patient. In various embodiments, the implantable device can be released from the tissue by being pulled away from the trapped portion of the tissue without using the push wire to operate the fixation mechanism (i.e., without deactivating the fixation mechanism), a method referred to as a "pull-out release". The implantable device can be configured to allow for the pull-out release without causing unacceptable tissue and/or device damage. For example, the amount of pulling force required for pulling the implantable device from the trapped portion of the tissue while the fixation mechanism remains activated (referred to as the "pull-out force") is to be small enough to prevent the implantable device from being broken inside the patient.

In various embodiments, the amount of the pull-out force can be experimentally determined and used as a constraint in the design of the fixation mechanism. The amount of the pull-out force is to be larger than the force required for preventing migration of the implantable device in the tissue but smaller than the pulling force that would cause the unacceptable tissue and/or device damages. For example, an excessive pull-out force can break the conduit of the implantable device, leaving a front portion of the device in the patient that may require surgical removal. Experiments with a prototype implantable device showed a pulling force of about 5 pounds could break the conduit, while a pulling force of about 1 pound is required to prevent the implantable device from an unacceptable degree of migration in the tissue. Thus, the fixation mechanism is to be designed to provide a pull-out force within the range of 2 to 4 pounds to allow for the pull-out release.

Figures 17A, 17B:
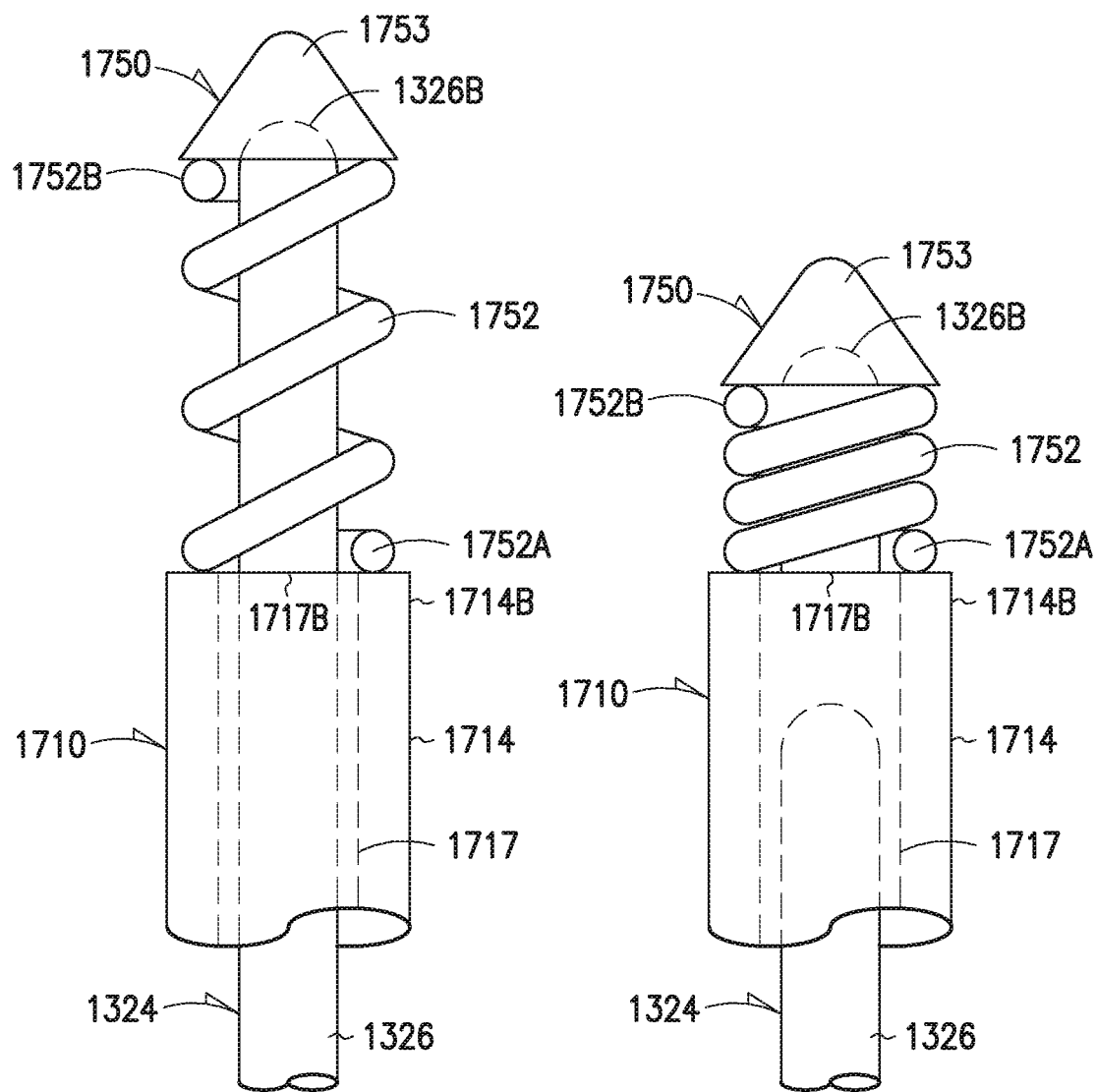
FIGS. 17A-17B are illustrations of a front end portion of an implantable device used with a push wire, where the implantable device includes a fixation mechanism including a spring, with FIG. 17A showing the spring in its extended position and FIG. 17B showing the spring in its resting position, according to an embodiment of present subject matter.

FIGS. 17A-17B are illustrations of a front end portion of an implantable device 1710 used with the push wire 1324, according to an embodiment of present subject matter. The implantable device 1710 can represent an example of implantable device 1310 includes a fixation mechanism 1750, which can represent an example of the fixation mechanism 1350. The front end portion of the implantable device 1710 as shown in FIG. 17 includes a front portion of an elongate conduit 1714 having a conduit front end 1714B. A push wire lumen 1717 extends longitudinally in the conduit 1714 and has a lumen front end 1717B.

The fixation mechanism 1750 includes a coil spring 1752 and a device tip 1753. FIG. 17A shows the spring 1752 in its extended position. FIG. 17B shows the spring 1752 in its resting position (i.e., natural length). The spring 1752 has a spring rear end 1752A coupled to the conduit front end 1714B and a spring front end 1752B. The device tip 1753 is coupled to the spring front end 1752B to receive the push wire front end 1326B to be pushed by the push wire 1324 in the forward direction for extending the spring 1752. The spring 1752 can anchor the implantable device 1710 to the tissue by being extended (as illustrated in FIG. 17A) to engage a portion of the tissue using the longitudinal movement of the push wire 1324 in the forward direction and returning to its resting position (as illustrated in FIG. 17B) to trap the engaged portion of the tissue using the longitudinal movement of the push wire 1324 in the reverse direction. Repetitive longitudinal movements of the push wire 1324 in the forward and reverse directions may be needed sometimes to reach a desirable stability of the anchoring. The spring 1752 can also release the implantable device 1710 from the tissue by expelling the trapped portion of the tissue using additional longitudinal movements of the push wire 1324 without re-trapping another portion of the tissue. To prevent the spring 1752 from engaging and trapping another portion of the tissue after the release, the implantable device 1710 can be moved away from the trapped portion of the tissue while keeping the spring 1752 in its extended position. In various embodiments, the implantable device 1710 can be released from the tissue by being pulled away from the trapped portion of the tissue without using the push wire 1324 (to extend the spring 1752) (the pull-out release). The implantable device 1710 can be configured to allow for the pull-out release without causing unacceptable tissue and/or device damage.

Figure 18A:
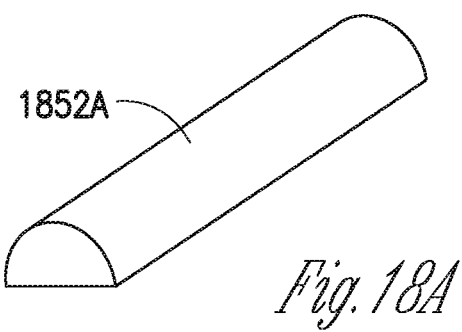
FIGS. 18A-18C are each an illustration of a wire used for making the spring of FIGS. 17A-17B, with FIG. 18A showing a wire with semicircular cross-section, FIG. 18B showing a wire with rectangular cross-section and dents, and FIG. 18C showing a wire with semicircular cross-section and bumps, according to various embodiments of present subject matter.
Figure 18B:
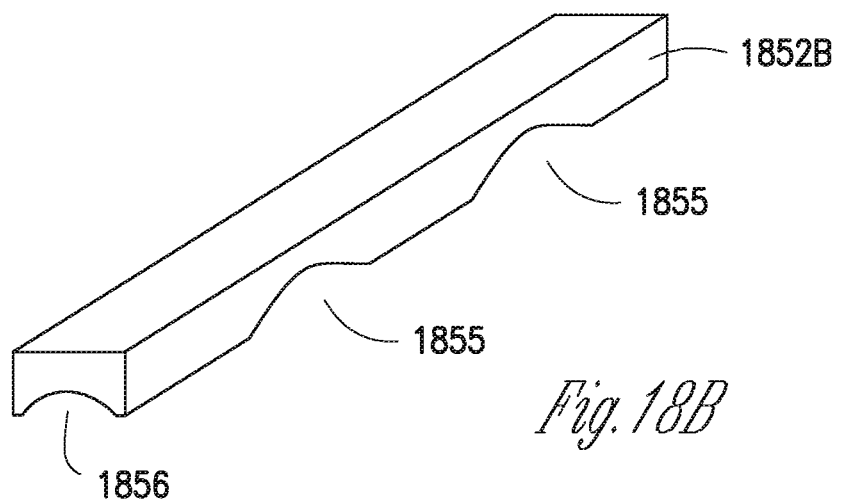
Figure 18C:
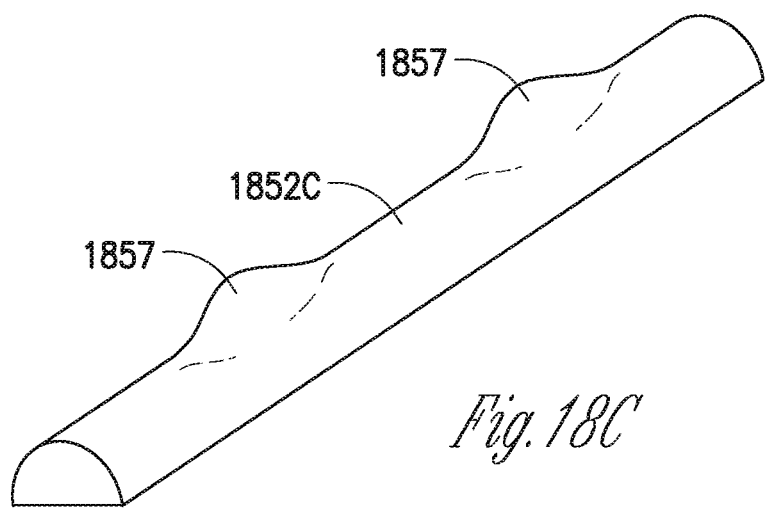

FIGS. 18A-18C are each an illustration of a wire used for making the spring 1752, according to various embodiments of present subject matter. In various embodiments, the spring 1752 is made of metal and includes multiple coils with space between the coils in the resting state to maintain viability of the portion of the tissue trapped in the spring 1752. In various embodiments, a metal wire is formed into the spring 1752. Examples of the metal wire include a wire 1852A as illustrated in FIG. 18A, a wire 1852B as illustrated in FIG. 18B, and a wire 1852C as illustrated in FIG. 18C. The metal wire 1852A has a semicircular cross-section. The flat side of a wire having a semicircular cross-section provides for better grip on tissue when compared to a wire having a circular cross-section. The metal wire 1852B has generally a rectangular cross-section with dents 1855 and/or 1856 on the wire to provide for the space between the coils. The rectangular cross-section of the wire prevents nesting of the coils when the spring is in its resting or compressed position. The metal wire 1852C has generally a semicircular cross-section with bumps 1857 on the wire to provide the space between the coils. Other examples of the metal wire include a metal wire having a circular cross-section and a braided wire. In various embodiments, the metal wire can have any cross-section and/or features that facilitate engaging a portion of the tissue in the extended position of the spring and/or trapping of the engaged portion of the tissue in the resting position of the spring, as well as maintaining viability of the trapped tissue in the resting position of the spring throughout the use of the implantable device.

In various other embodiments, the spring 1752 may also be a lattice-cut tube (e.g., a structure similar to an intravascular stent) or a high durometer spiral-cut silicone tube. The spring 1752 can be any structure that is biocompatible and can engage and trap the portion of the tissue using one or more cycles of extension and returning to resting position.

Figure 19:
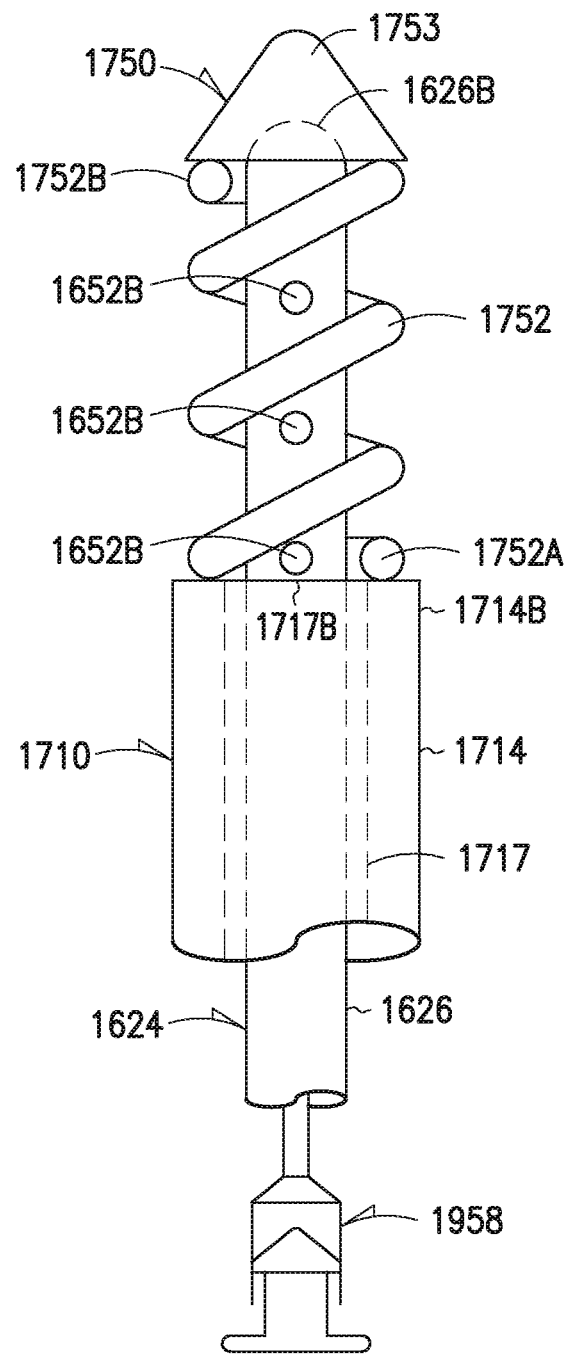
FIG. 19 is an illustration of the front end portion of the implantable device of FIG. 17 used with another push wire, according to an embodiment of present subject matter.

FIG. 19 is an illustration of a front end portion of the implantable device 1710 used with the push wire 1624, according to an embodiment of present subject matter, according to an embodiment of present subject matter. FIG. 19 differs from FIG. 17 in that the push wire 1624 replaces the push wire 1324 in FIG. 17. The push wire 1624 is used to facilitate the engaging of the portion of the tissue into the spring 1752 during the anchoring of the implantable device 1710 to the tissue, and/or to facilitate the expelling of the portion of the tissue from the spring during the release of the implantable device 1710 from the tissue, when the spring is extended using the push wire 1624. During the anchoring, a syringe 1958 can be used to draw fluid (e.g., air) through the front openings 1652B of the core lumen 1652 of the push wire 1624. This lowers the pressure in the lumen 1652, which draws additional tissue into the space between the coils of the spring 1752. During the release, the syringe 1958 can be used to inject fluid (e.g., saline) through the front openings 1652B of the core lumen 1652 of the push wire 1624. This expels the portion of the tissue in the space between the coils of the spring 1752 from the spring 1752.

FIGS. 20A-20C are illustrations of a front end portion of an implantable device 2010 used with a push wire 2024, according to an embodiment of present subject matter. The implantable device 2010 can represent an example of implantable device 1310 including a fixation mechanism 2050, which can represent another example of the fixation mechanism 1350. The front end portion of the implantable device 2010 as shown in FIG. 20 includes a front portion of an elongate conduit 2014 having a conduit front end 2014B. A push wire lumen 2017 extends longitudinally in the conduit 2014 and has a lumen front end 2017B. The push wire 2024 can represent an example of the push wire 1324 having an elongate push wire body 2026 and a push wire front end 2026B that is configured to operate the fixation mechanism 2050.

The fixation mechanism 2050 includes pincers 2064 coupled to the conduit front end 2014B. FIG. 20A is a cross-sectional side view showing the pincers 2064 open. FIG. 20B is a cross-sectional side view showing the pincers 2064 closed. FIG. 20C is an end view showing the pincers 2064 closed. The pincers 2064 can anchor the implantable device 2010 to the tissue by being opened (as illustrated in FIG. 20A) to engage a portion of the tissue using longitudinal movement of the push wire 2024 in the forward direction and being closed (as illustrated in FIG. 20B) to trap the engaged portion of the tissue using longitudinal movement of the push wire 2024 in the reverse direction. The pincers 2064 can also release the implantable device 2010 from the tissue by expelling the trapped portion of the tissue using additional longitudinal movements of the push wire 2024 without re-trapping another portion of the tissue. To prevent the pincers 2064 from engaging and trapping another portion of the tissue after the release, the implantable device 2010 can be moved away from the trapped portion of the tissue while the pincers 2064 are open. In various embodiments, the implantable device 2010 can be released from the tissue by being pulled away from the trapped portion of the tissue without using the push wire 2024 (the pull-out release). The implantable device 2010 can be configured to allow for the pull-out release without causing unacceptable tissue and/or device damage.

The push wire front end 2026B is shaped to be suitable for opening the pincers 2064. In various embodiments, the pincers 2064 can include a radiopaque material, such as tantalum or Nitinol (alloy of nickel and titanium), to function as a marker on X-ray.

1.2. Using Rotational Movements of Push Wire

In various embodiments, the fixation mechanism can anchor the implantable device to the tissue (i.e., be activated) by rotating the push wire in a tightening rotational direction. In various further embodiments, the fixation mechanism can also release the implantable device from the tissue (i.e., be deactivated) by rotating the push wire in a loosening rotational direction. In one embodiment, the tightening rotational direction is a clockwise direction, and the loosening rotational direction is a counterclockwise direction. In another embodiment, the tightening rotational direction is a counterclockwise direction, and the loosening rotational direction is a clockwise direction. In various embodiments, the implantable device can be released from the tissue by being pulled away from the trapped portion of the tissue without using the push wire to operate the fixation mechanism (i.e., the pull-out release, without deactivating the fixation mechanism). The implantable device can be configured to allow for the pull-out release without causing unacceptable tissue and/or device damage. For example, the amount of force required for pulling the implantable device from the trapped portion of the tissue while the fixation mechanism remains activated is to be small enough to prevent the implantable device from being broken inside the patient.

Figure 21:
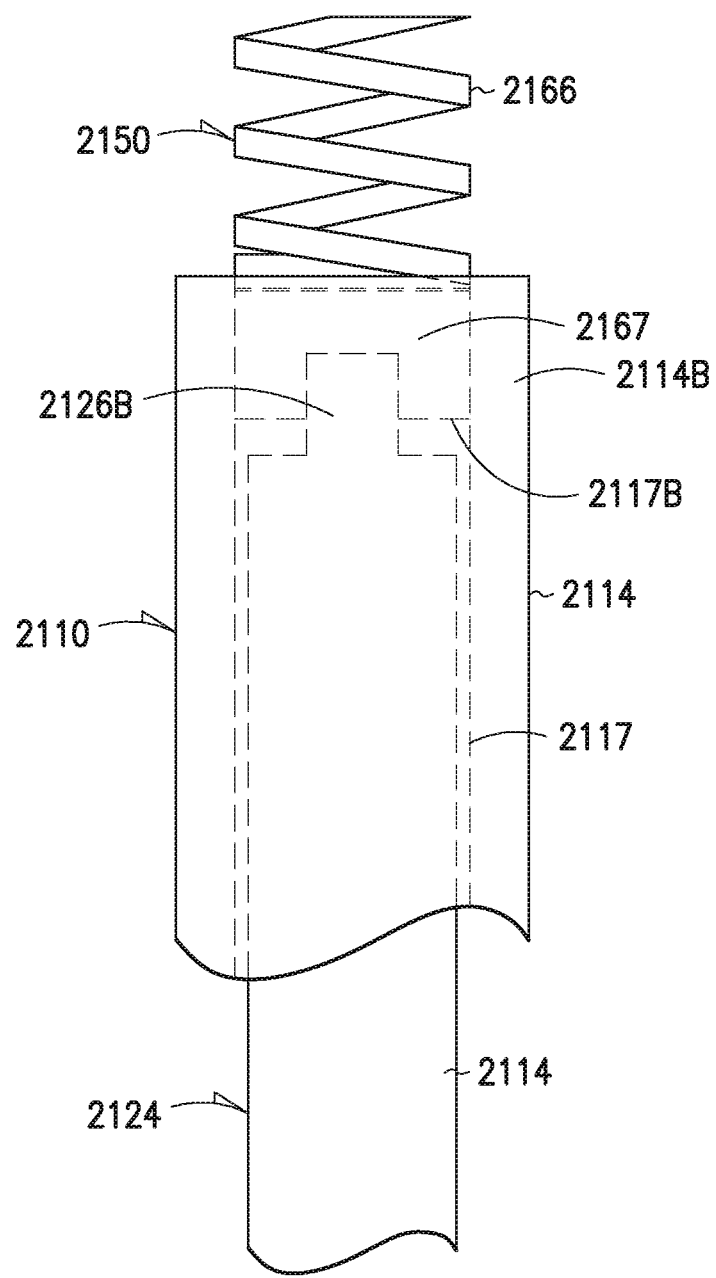
FIG. 21 is an illustration of a front end portion of an implantable device used with a push wire, where the implantable device includes a fixation mechanism including a helix, according to an embodiment of present subject matter.

FIG. 21 is an illustration of a front end portion of an implantable device 2110 used with a push wire 2124, according to an embodiment of present subject matter. The implantable device 2110 can represent an example of the implantable device 1310 or 1410 and includes a fixation mechanism 2150, which can represent another example of the fixation mechanism 1350 or 1450. The front end portion of the implantable device 2110 as shown in FIG. 21 includes a front portion of an elongate conduit 2114 having a conduit front end 2114B. A lumen 2117, which can represent an example of the push wire lumen 1317 or the inflation lumen 1415, extends longitudinally in the conduit 2114 and has a lumen front end 2117B. The push wire 2124 can represent an example of the push wire 1324 having an elongate push wire body 2126 and a push wire front end 2126B that is configured to operate the fixation mechanism 2150.

The fixation mechanism 2150 is a helix assembly that can include a base 2167 and a helix 2166 coupled to the base 2167. The base 2167 is coupled to the lumen 2117 at the conduit front end 2114B and configured to engage the push wire 2124 at the push wire front end 2126B. The implantable device 2110 can be anchored to the tissue by rotating the push wire 2124 (engaged to the base 2167) in the tightening rotational direction such that the helix 2166 enters the tissue. After being anchored, the implantable device 2110 can be released from the tissue by rotating the push wire 2124 in the loosening rotational direction. In some embodiments, the helix 2166 is configured to allow the implantable device 2110 to be released from the tissue by simply pulling the implantable device 2110 from the tissue (the pull-out release). For example, the helix 2166 can include a number of turns and/or be sized to limit the anticipated damage to the tissue and/or the implantable device 2110 caused by the pull-out release to an acceptable extent. In various embodiments, the helix 2166 include a number of turns determined to allow for control of the amount of pull-out force by controlling the extent of the tightening rotational movement. The amount of the pull-out force depends on the type of tissue to which the implantable device is to be anchored on (e.g., fat, muscle, or scar tissue) and hence, can differ from patient to patient. During the implantation procedure, the physician performing the procedure can decide the number of turns of the helix 2166 that actually enters the tissue, for example by making the tightening rotational movement incrementally while pulling the implantable device to feel for the pull-out force.

In various embodiments, the base 2167 can be coupled to the lumen 2117 in a fluid-tight manner to allow the implantable device 2110 to be a single-lumen implantable device in which the lumen 2117 functions as both the push wire lumen and the inflation lumen. In various other embodiments, the base 2167 can be coupled to the push wire lumen of a multi-lumen implantable device that includes a separate inflation lumen.

Examples of the implantable device 2110 with the fixation device 2150 are discussed below with reference to FIGS. 22-24. In various embodiments, considerations in choosing material(s) for constructing the fixation device 2150 (including its various examples discussed below with reference to FIGS. 22-24) can include, for example, biocompatibility for long-terns implantation, magnetic resonance imaging (MRI) safety, radiopacity, and resistance to galvanic corrosion when more than one material is used. Examples of suitable materials include titanium, nitinol (nickel-titanium), tantalum, and platinum-iridium.

1.2.1. Helix with Base Rotating in Threaded Sleeve

Figure 22A:
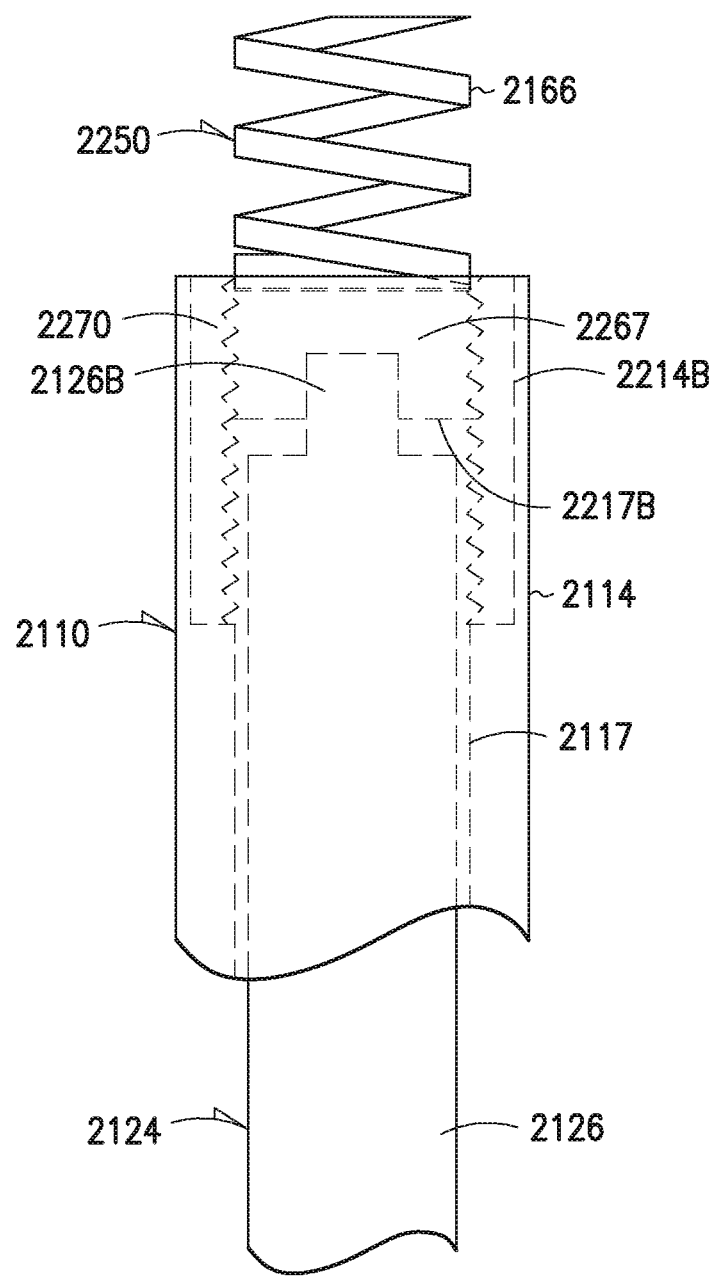
FIG. 22A-22B are illustrations of an example of the front end portion of the implantable device used with the push wire of FIG. 21, with FIG. 22A being a top view with the implantable device being a single-lumen device or a multi-lumen device and FIG. 22B being a side view with the implantable device being a multi-lumen device, according to an embodiment of present subject matter.

FIG. 22A is an illustration of a front end portion of an implantable device 2210 used with the push wire 2124, according to an embodiment of present subject matter. The implantable device 2210 can represent an example of implantable device 2110 and includes a fixation mechanism 2250, which is a helix assembly and can represent an example of the fixation mechanism 2150. The front end portion of the implantable device 2210 as shown in FIG. 22A includes a front portion of an elongate conduit 2214 having a conduit front end 2214B. A lumen 2217, which can function as a push wire lumen (e.g., the push wire lumen 1317) or function as both the push wire lumen and the inflation lumen (e.g., the inflation lumen 1415), extends longitudinally in the conduit 2214 and has a lumen front end 2217B. The push wire 2124 can represent an example of the push wire 1324 having the elongate push wire body 2126 and the push wire front end 2126B that is configured to operate the fixation mechanism 2250.

The conduit 2214 includes a threaded sleeve 2270 affixed onto the surface of the lumen 2217 at the conduit front end 2214B. The fixation mechanism 2250 includes a threaded base 2267 and a helix 2266 coupled to the threaded base 2267. The threaded base 2267 and the threaded sleeve 2270 are configured to mate each other to allow the threaded based 2267 to move longitudinally by rotating within the threaded sleeve 2270. The threaded base 2267 is configured to engage the push wire 2124 at the push wire front end 2126B for the helix 2266 to exit from the lumen 2217 and enter the tissue by rotating the push wire 2124 in the tightening rotational direction and for the helix 2266 to be released from the tissue and retract into the lumen 2217 by rotating the push wire 2124 in the loosening rotational direction. The helix 2266 can also be configured to allow for its release from the tissue by simply pulling the implantable device 2210 (the pull-out release) from the tissue without causing unacceptable damage to the tissue and/or the implantable device 2210. The threaded sleeve 2270 can be sized and positioned in the conduit 2214 to allow the helix 2266 to be entirely inside the conduit 2214. When desirable, this allows the helix 2266 to be kept from the outer surface of the implantable device 2210 during its insertion into the patient.

In various embodiments, the threaded base 2267 and the threaded sleeve 2270 can be configured in a fluid-tight manner to allow the implantable device 2210 to be a single-lumen implantable device in which the lumen 2217 functions as both the push wire lumen and the inflation lumen. In various other embodiments, the threaded sleeve 2270 can be affixed to the push wire lumen of a multi-lumen implantable device in which the lumen 2217 is the push wire lumen (which is separate from the inflation lumen).

Figure 22B:
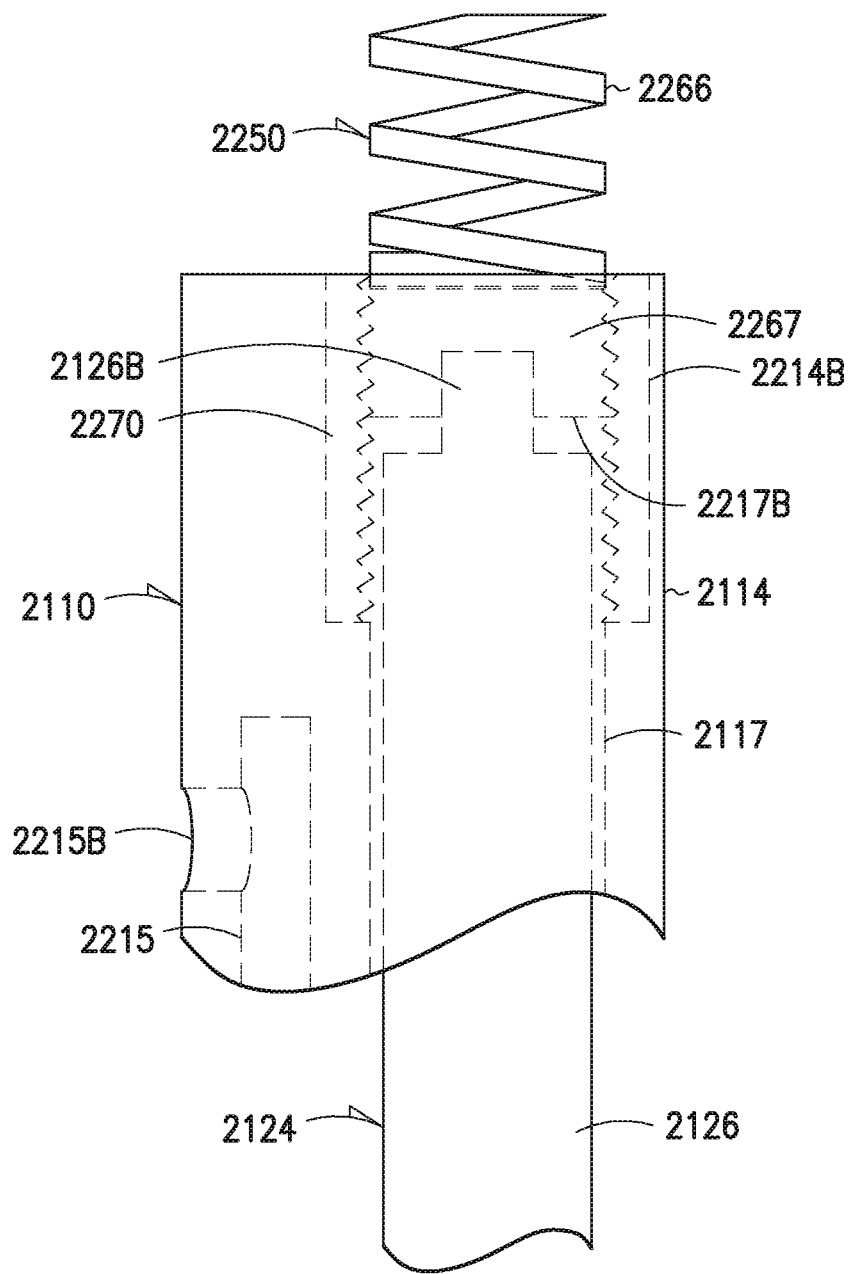

FIG. 22B is another illustration of the front end portion of an implantable device 2210 used with the push wire 2124, according to an embodiment of present subject matter. FIG. 22A can be seen as a top view illustration of the front end portion of the implantable device 2210 with the implantable device 2210 being either the single-lumen implantable device or the multi-lumen implantable device. FIG. 22B can be seen as a side-view illustration of the front end portion of the implantable device 2210 that shows an inflation lumen 2215 having a lumen front opening 2215B in fluid communication with the chamber of the adjustable membrane element (not shown) of the implantable device 2210. The inflation lumen 2115 is fluid-tight by either ending within the conduit 2214 by manufacturing or plugged at the conduit front end 2214B.

1.2.2. Helix with Base Rotative in Bushing

Figure 23:
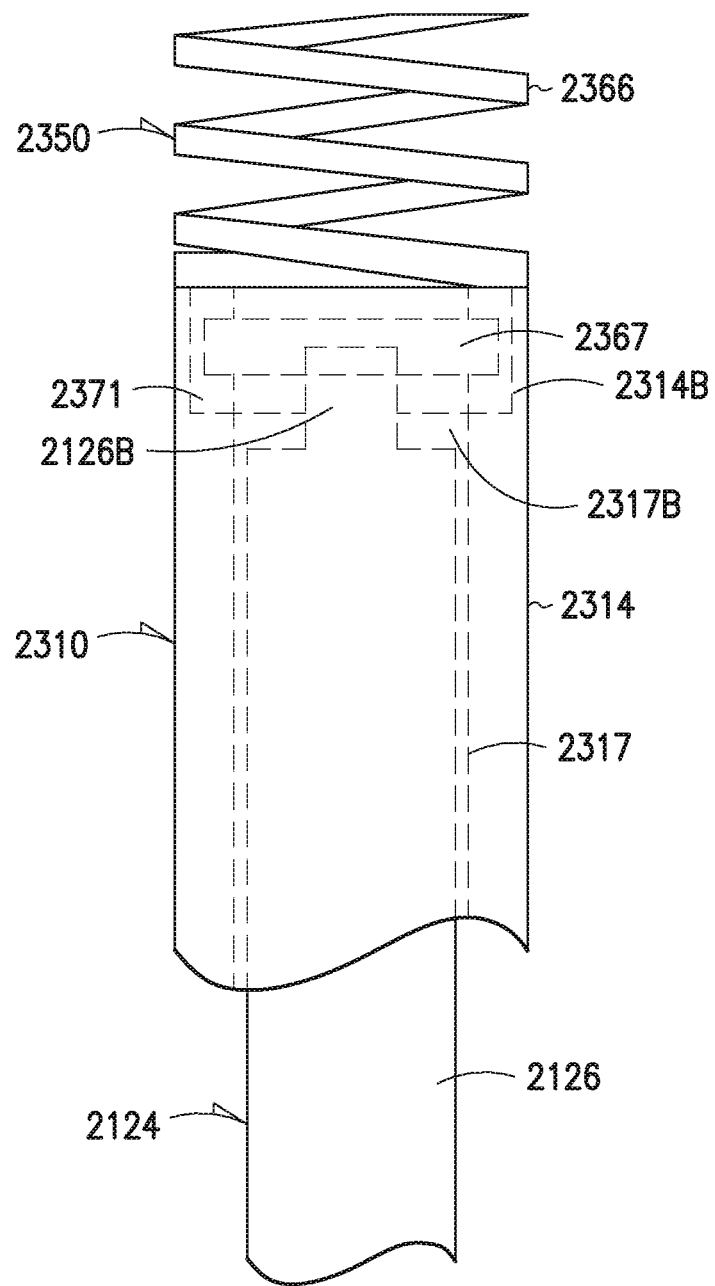
FIG. 23 is an illustration of another example of the front end portion of the implantable device used with the push wire of FIG. 21, according to an embodiment of present subject matter.

FIG. 23 is an illustration of a front end portion of an implantable device 2310 used with the push wire 2124, according to an embodiment of present subject matter. The implantable device 2310 can represent another example of implantable device 2110 and includes a fixation mechanism 2350, which is a helix assembly and can represent another example of the fixation mechanism 2150. The front end portion of the implantable device 2310 as shown in FIG. 23 includes a front portion of an elongate conduit 2314 having a conduit front end 2314B. A lumen 2317, which can function as a push wire lumen (e.g., the push wire lumen 1317) or function as both the push wire lumen and the inflation lumen (e.g., the inflation lumen 1415), extends longitudinally in the conduit 2314 and has a lumen front end 2317B. The push wire 2124 can represent an example of the push wire 1324 having the elongate push wire body 2126 and the push wire front end 2126B that is configured to operate the fixation mechanism 2350.

The conduit 2314 includes a bushing 2371 affixed onto the surface of the lumen 2317 at the conduit front end 2314B. The fixation mechanism 2350 includes a base 2367 and a helix 2366 coupled to the base 2367. The base 2367 is configured to allow the base 2367 to rotate within the bushing 2371 without longitudinal movement of the fixation mechanism 2350 relative to the conduit 2314. The base 2367 is configured to engage the push wire 2124 at the push wire front end 2126B for the helix 2366 to enter the tissue by rotating the push wire 2124 in the tightening rotational direction and for the helix 2366 to be released from the tissue by rotating the push wire 2124 in the loosening rotational direction. The helix 2366 can also be configured to allow for its release from the tissue by simply pulling the implantable device 2310 from the tissue (the pull-out release) without causing unacceptable damage to the tissue and/or the implantable device 2310. The fixation mechanism 2350 can be configured for the helix 2366 to be positioned completely or substantially outside of the conduit 2314. The diameter of the helix 2366 is not limited by the diameter of the lumen 2317. In the illustrated embodiment, the diameter of the helix 2366 is larger than the diameter of the lumen 2317, and can be substantially identical to the diameter of the conduit 2314 when the lumen front end 2317B is centered at the front end of conduit 2314. In various embodiments, the diameter of the helix 2366 can be larger than, substantially equal to, or smaller than the diameter of the lumen 2317, and can be determined based on an amount of force for holding the implantable device 2310 in place after the implantation.

In various embodiments, the base 2367 and the bushing 2371 can be configured in a fluid-tight manner to allow the implantable device 2310 to be a single-lumen implantable device in which the lumen 2317 functions as both the push wire lumen and the inflation lumen. In various other embodiments, the bushing 2371 can be affixed to the push wire lumen of a multi-lumen implantable device in which the lumen 2317 functions as the push wire lumen in addition to the inflation lumen. The relative positions of the push wire lumen and the inflation lumen in these multi-lumen embodiments of the implantable device 2310 can be the same as or similar to what is illustrated in FIG. 22B for the implantable device 2210.

1.2.3. Helix with Base Fixed to Implantable Device

Figure 24:
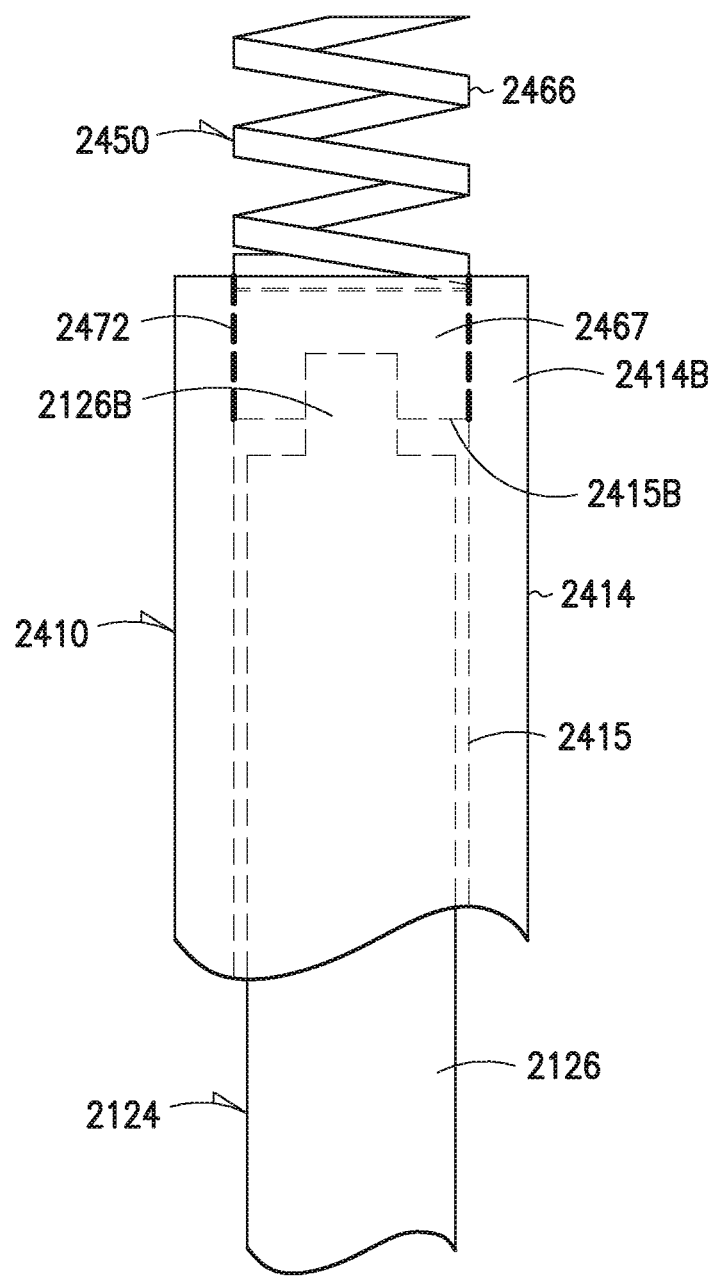
FIG. 24 is an illustration of yet another illustration of an example of the front end portion of the implantable device used with the push wire of FIG. 21, according to an embodiment of present subject matter.

FIG. 24 is an illustration of a front end portion of an implantable device 2410 used with the push wire 2124, according to an embodiment of present subject matter. The implantable device 2410 can represent another example of implantable device 2110 and includes a fixation mechanism 2450, which is a helix assembly and can represent another example of the fixation mechanism 2150. The front end portion of the implantable device 2410 as shown in FIG. 24 includes a front portion of an elongate conduit 2414 having a conduit front end 2414B. A lumen 2417, which can function as a push wire lumen (e.g., the push wire lumen 1317) or function as both the push wire lumen and the inflation lumen (e.g., the inflation lumen 1415), extends longitudinally in the conduit 2414 and has a lumen front end 2417B. The push wire 2124 can represent an example of the push wire 1324 having the elongate push wire body 2126 and the push wire front end 2126B that is configured to operate the fixation mechanism 2450.

The fixation mechanism 2450 includes a base 2467 and a helix 2466 coupled to the base 2467. The base 2467 is affixed to the lumen 2417 at the conduit front end 2414B through an affixation 2472 (e.g., an adhesive layer). The base 2467 is configured to engage the push wire 2124 at the push wire front end 2126B for the helix 2466 to enter the tissue by rotating the push wire 2124 in the tightening rotational direction and for the helix 2466 to be released from the tissue by rotating the push wire 2124 in the loosening rotational direction. Because the base 2467 is affixed to the lumen 2417, when the push wire 2124 is engaged to the base 2467 and rotated, the entire implantable device 2410 rotates with the helix 2466. The helix 2466 can also be configured to allow for its release from the tissue by simply pulling the implantable device 2410 from the tissue (the pull-out release) without causing unacceptable damage to the tissue and/or the implantable device 2410. The diameter of the helix 2466 is not limited by the diameter of the lumen 2417. In the illustrated embodiment, the diameter of the helix 2466 is substantially identical to the diameter of the lumen 2417. In various embodiments, the diameter of the helix 2466 can be larger than, substantially equal to, or smaller than the diameter of the lumen 2417, and can be determined based on an amount of force for holding the implantable device 2410 in place after the implantation.

In various embodiments, the affixation 2472 can affix and seal the base 2467 to the lumen 2417 in a fluid-tight manner to allow the implantable device 2410 to be a single-lumen implantable device in which the lumen 2417 functions as both the push wire lumen and the inflation lumen. In various other embodiments, the base 2467 can be affixed to the push wire lumen of a multi-lumen implantable device in which the lumen 2417 functions as the push wire lumen in addition to the inflation lumen. The relative positions of the push wire lumen and the inflation lumen in these multi-lumen embodiments of the implantable device 2410 can be the same as or similar to what is illustrated in FIG. 22B for the implantable device 2210. When compared to the multi-lumen implantable device, the single-lumen implantable device allows for the push wire lumen to have a larger diameter, thereby accommodating a push wire of a larger diameter. The push wire having the larger diameter can provide more torque for rotating the implantable device 2410 during anchoring or release. In various embodiments in which the implantable device 2410 is a single-lumen implantable device (e.g., an example of the implantable device 1410), the implantable device 2410 can be removed from the patient by (1) using the push wire 2124 reinserted through the septum (e.g., the septum 1418) to rotate in the loosening rotational direction, thereby leaving the implantable device 2410 intact, (2) cutting off the rear port (e.g., the rear port 1416) and using the push wire 2124 reinserted directly into the lumen 2417 to rotate in the loosening rotational direction, or (3) pulling the implantable device 2410 out without using the push wire 2124 (the pull-out release).

2. To Anchor/Release Via Lumen

In various embodiments, a fixation mechanism (e.g., fixation mechanism 1350 or 1450) can anchor an implantable device (e.g., implantable device 1310 or 1410) to the tissue by receiving an energy transmitted using a lumen (e.g., the push wire lumen 1315 of implantable device 1310, the inflation lumen 1415 of the implantable device 1410, the core lumen 1552 of the push wire 1524, or the core lumen 1652 of the push wire 1624). In various further embodiments, the fixation mechanism can also release the implantable device from the tissue by receiving another energy transmitted using the lumen. In various embodiments, the fixation mechanism can be hydraulically controllable (e.g., hydraulically activated and/or hydraulically deactivated) by passing one or more fluids via the lumen.

2.1. Using Pressure Transmitted Via Lumen

In various embodiments, the anchoring of the implantable device to the tissue can be facilitated by drawing a fluid from a lumen of the implantable device or a push wire that provides for access to a portion of the tissue, thereby creating a low pressure or vacuum to engage that portion of the tissue into the fixation mechanism to be trapped in the fixation mechanism. The lumen has one or more front openings allowing for access to the tissue. Examples of such a lumen includes a push wire lumen of the implantable device that includes one or more front openings and a core lumen of a hollow-core push wire that includes one or more front openings. In various further embodiments, the release the implantable device from the tissue can also be facilitated by injecting a fluid into the lumen, thereby creating a hydraulic pressure to expel the trapped portion of the tissue from the fixation mechanism. A syringe can be coupled to the lumen to draw the fluid from the lumen or to inject the fluid into the lumen.

This pressure method can be used in conjunction with another fixation method that is configured to anchor the implantable device to the tissue by engaging a portion of the tissue into the fixation mechanism and trapping the engaged portion of the tissue using the push wire, and to release the implantable device from the tissue by expelling the trapped portion of the tissue using the push wire, to facilitate the engaging and the expelling of the portion of the tissue. One example is discussed above with reference to FIG. 19.

2.2. Using Energy Transmitted Via Lumen

In various embodiments, the fixation mechanism can anchor the implantable device to the tissue by receiving a liquid via the lumen. The liquid causes a thermal or chemical response of the fixation mechanism to engage a portion of the tissue into the fixation mechanism to be trapped in the fixation mechanism. In various further embodiments, the fixation mechanism can also release the implantable device from the tissue by receiving another liquid via the lumen. The liquid causes another thermal or chemical response of the fixation mechanism to expel the trapped portion of the tissue from the fixation mechanism. A syringe can be coupled to the lumen inject the liquid.

In one embodiment, the fixation mechanism includes pincers that can anchor the implantable device to the tissue by opening to receive a portion of the tissue in response to delivery of a liquid having a hot temperature exceeding an opening threshold temperature, and closing to trap the received portion of the tissue in response to delivery of a liquid having a cold temperature under a closing threshold temperature. One embodiment includes the implantable device 2010, as illustrated in FIG. 20, with the pincers 2064 made of thermally controllable material, such that the state of the pincers 2064 can be controlled by varying their temperature, in place of or in addition to using the push wire 2024. In this embodiment, the pincers 2064 open in response to a hot liquid being injected into the lumen and close in response to a cold liquid being injected into the lumen. The liquid having the hot temperature and the liquid having the cold temperature can be a common liquid (e.g., saline) at different temperatures.

Fixation Method Examples

Figure 25:
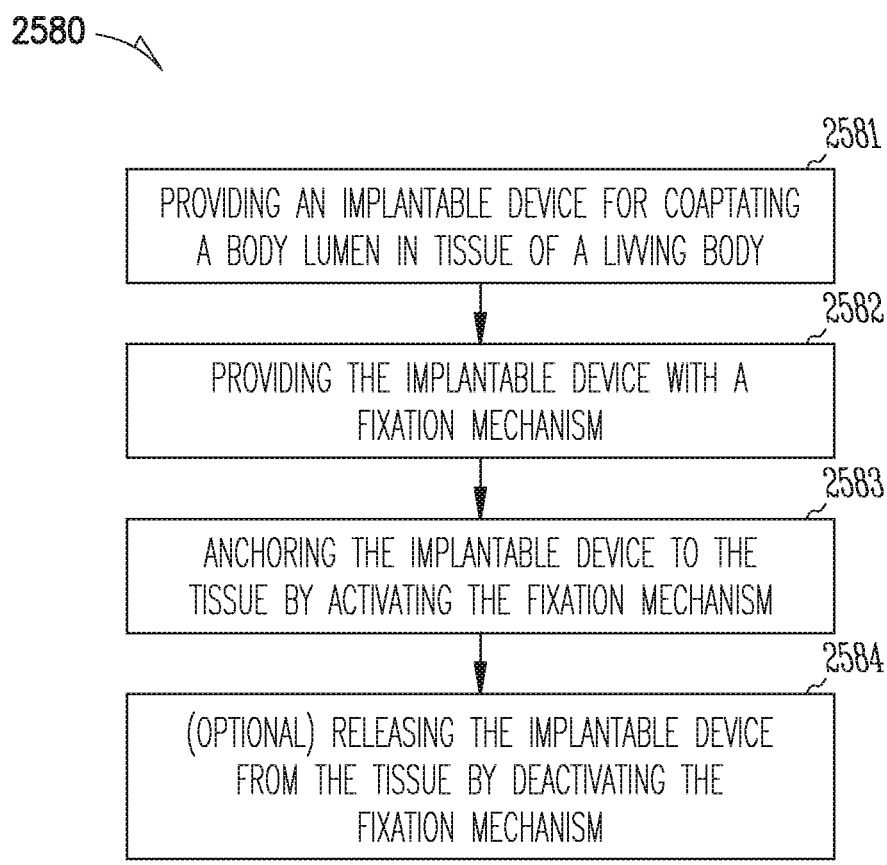
FIG. 25 is a flow chart illustrating a method for anchoring an implantable device to tissue, according to an embodiment of present subject matter.

FIG. 25 is a flow chart illustrating a method 2580 for anchoring an implantable device to tissue, according to an embodiment of present subject matter. In various embodiments, the implantable device provides for controllable coaptation of a body lumen in tissue of a living body, such as to treat urinary incontinence of a patient. Examples of the implantable devices include, but are not limited to, all the implantable devices including their various embodiments as discussed in this document (e.g., implantable devices 110, 910, 1010, 1310, 1410, 1710, 2010, 2110, 2210, 2310, and 2410). By way of example, but not by way of limitation, the method 2580 as discussed below can use a push wire (that is used as a surgical tool for placing the implantable device) to operate a fixation mechanism, including its activation and optionally deactivation.

At 2581, an implantable device is provided. The implantable device includes an adjustable membrane element (also referred to as a balloon) and an elongate conduit. The adjustable membrane element includes a continuous wall having an inner surface defining a chamber. The elongate conduit includes a conduit peripheral surface, a conduit rear end, a conduit front end, and a push wire lumen. The conduit peripheral surface is connected to and sealed to the adjustable membrane element at or near the conduit front end. The push wire lumen extends longitudinally in the conduit and has an inlet to receive a portion of the push wire and a diameter suitable for accommodating the received portion of the push wire. The implantable device can also include a rear port permanently or detachably coupled to the conduit at the conduit rear end. Examples of the implantable device provided at 2281 can include, but are not limited to, implantable devices 110, 910, and 1010 and their various embodiments as discussed in this document.

At 2582, the implantable device is provided with the fixation mechanism to limit displacement of the implantable device after being implanted in the tissue. Thus, the implantable device also includes the fixation mechanism. Examples of such an implantable device can include, but are not limited to, implantable devices 1310, 1410, 1710, 2010, 2110, 2210, 2310, 2410 and their various embodiments as discussed in this document.

At 2583, the implantable device is anchored to the tissue by activating the fixation mechanism. In various embodiments, the implantable device may need to be re-positioned in the tissue to improve efficacy of the treatment or removal from the tissue. Thus, optionally at 2584, the implantable device is released from the tissue by deactivating the fixation mechanism. In some embodiments, the implantable device can be released from the tissue by pulling the implantable device without deactivating the fixation mechanism (the pull-out release). In such embodiments, the fixation mechanism is configured to limit possible damage to the tissue and/or the implantable device to an acceptable extent. For example, the anchoring force is to be limited to an amount that will not break the conduit of the implantable device when the implantable device is being pulled.

In various embodiments, the implantable device is anchored to the tissue at 2583 by activating the fixation mechanism to trap a portion of the tissue in the fixation mechanism. The implantable device is released from the tissue at 2584 by deactivating the fixation mechanism to release the trapped portion of the tissue from the fixation mechanism or by simply pulling the implantable device (the pull-out release). In various other embodiments, the implantable device is anchored to the tissue at 2583 by activating the fixation mechanism to extend an anchoring member of the fixation mechanism into the tissue. The implantable device is released from the tissue at 2584 by deactivating the fixation mechanism to retract the anchoring member of the fixation mechanism from the tissue or by simply pulling the implantable device (the pull-out release).

In various embodiments, an energy is transmitted using the push wire to activate the fixation mechanism at 2583. Optionally, another energy is transmitted using the push wire to deactivate the fixation mechanism at 2584. The energy transmitted at 2583 and the energy transmitted at 2584 can include the same type of energy or different types of energy. In one embodiment, the fixation mechanism is activated using longitudinal movements of the push wire and optionally deactivated using additional longitudinal movements of the push wire. In another embodiment, the fixation mechanism is activated using a rotational movement of the push wire in a rotational direction and optionally deactivated the using a rotational movement of the push wire in an opposite rotational direction. In yet another embodiment, the fixation mechanism is activated by delivering a non-mechanical energy to the fixation mechanism using the push wire and optionally deactivated delivering another non-mechanical energy to the fixation mechanism using the push wire. In these embodiments, the deactivation of the fixation mechanism is optional, and the implantable device can be released by simply pulling the implantable device (the pull-out release) without deactivating the fixation mechanism.

In various embodiments, a fluid is passed through a lumen to activate the fixation mechanism at 2583. Optionally, another fluid is passed using the lumen to deactivate the fixation mechanism at 2584. The lumen can be the push wire lumen of the conduit of the implantable device and/or a core lumen of the push wire. In these embodiments, the deactivation of the fixation mechanism is optional, and the implantable device can be released by simply pulling the implantable device (the pull-out release) without deactivating the fixation mechanism.

This application is intended to cover adaptations or variations of the present subject matter. It is to be understood that the above detailed description is intended to be illustrative, and not restrictive. Other embodiments will be apparent to those of skill in the art upon reading and understanding the above description. The scope of the present subject matter should be determined with reference to the appended claims, along with the full scope of legal equivalents to which such claims are entitled.

What is claimed is:

1. An implantable device configured to be positioned in tissue of a living body using a push wire for coaptation of a body lumen of the living body, the implantable device comprising:
    an adjustable membrane element including a continuous wall having an inner surface defining a chamber;
    an elongate conduit including a conduit peripheral surface, a conduit rear end, a conduit front end, and a push wire lumen, the conduit peripheral surface connected to and sealed to the adjustable membrane element at or near the conduit front end, the push wire lumen extending longitudinally in the conduit and having an inlet to receive a portion of the push wire and a diameter suitable for accommodating the received portion of the push wire; and
    a fixation mechanism configured to anchor the implantable device to the tissue and to be operated using longitudinal movements of the push wire, the fixation mechanism including:
        a spring including a spring front end and a spring rear end, the spring rear end coupled to the conduit front end, the spring configured to be extended to engage a portion of the tissue using a forward longitudinal movement of the push wire resulting from pushing the push wire toward the conduit front end and to contract to trap the engaged portion of the tissue using a reverse longitudinal movement of the push wire resulting from pulling the push wire in a direction opposite to a direction of the forward longitudinal movement, the spring including multiple coils with space between the coils to maintain viability of the portion of the tissue trapped in the spring; and
        a device tip coupled to the spring front end to be pushed by the push wire during the forward longitudinal movement of the push wire,
    wherein the implantable device is configured for implantation within the tissue with the adjustable membrane element adjacent the body lumen to provide volume to the tissue for adjustable coaptation to the body lumen.

2. The implantable device of claim 1, wherein the fixation mechanism is configured to allow the implantable device to be released from the tissue by expelling the trapped portion of the tissue using additional longitudinal movements of the push wire.

3. The implantable device of claim 1, wherein the fixation mechanism is configured to allow the implantable device to be released from the tissue by pulling the implantable device.

4. The implantable device of claim 1, further comprising:
    an inflation lumen extending longitudinally in the conduit in addition to and separate from the push wire lumen, the inflation lumen including a rear opening at the conduit rear end, a front opening in fluid communication with the chamber of the adjustable membrane element for adjustably expanding or contracting the adjustable membrane element by a flowable material introduced through the rear opening; and
    a rear port connected to the conduit at the conduit rear end, the rear port including a cavity and an elastic septum configured to seal the cavity, the cavity configured to contain the flowable material and being in fluid communication with the inflation lumen through the rear opening of the inflation lumen.

5. The implantable device of claim 1, wherein the push wire lumen comprises the inlet being a rear opening at the conduit rear end and a front opening in fluid communication with the chamber of the adjustable membrane element for adjustably expanding or contracting the adjustable membrane element by a flowable material introduced through the rear opening, and further comprising:
    a rear port connected to the conduit at the conduit rear end, the rear port including a cavity and an elastic septum configured to seal the cavity, the cavity configured to contain the flowable material and being in fluid communication with the inflation lumen through the rear opening of the push wire lumen.

6. An implantable device configured to be positioned in tissue of a living body using a push wire for coaptation of a body lumen of the living body, the implantable device comprising:
an adjustable membrane element including a continuous wall having an inner surface defining a chamber;
an elongate conduit including a conduit peripheral surface, a conduit rear end, a conduit front end, and a push wire lumen, the conduit peripheral surface connected to and sealed to the adjustable membrane element at or near the conduit front end, the push wire lumen extending longitudinally in the conduit and having an inlet to receive a portion of the push wire and a diameter suitable for accommodating the received portion of the push wire; and
a fixation mechanism configured to anchor the implantable device to the tissue and to be operated using longitudinal movements of the push wire, the fixation mechanism including pincers coupled to the conduit front end and configured to be opened to engage the portion of the tissue using a forward longitudinal movement of the push wire resulting from pushing the push wire toward the conduit front end and to be closed to trap the engaged portion of the tissue using a reverse longitudinal movement of the push wire resulting from pulling the push wire in a direction opposite to a direction of the forward longitudinal movement,
wherein the implantable device is configured for implantation within the tissue with the adjustable membrane element adjacent the body lumen to provide volume to the tissue for adjustable coaptation to the body lumen.

7. The implantable device of claim 6, wherein the fixation mechanism is configured to allow the implantable device to be released from the tissue by expelling the trapped portion of the tissue using additional longitudinal movements of the push wire.

8. The implantable device of claim 6, wherein the fixation mechanism is configured to allow the implantable device to be released from the tissue by pulling the implantable device.

9. The implantable device of claim 6, further comprising:
an inflation lumen extending longitudinally in the conduit in addition to and separate from the push wire lumen, the inflation lumen including a rear opening at the conduit rear end, a front opening in fluid communication with the chamber of the adjustable membrane element for adjustably expanding or contracting the adjustable membrane element by a flowable material introduced through the rear opening; and
a rear port connected to the conduit at the conduit rear end, the rear port including a cavity and an elastic septum configured to seal the cavity, the cavity configured to contain the flowable material and being in fluid communication with the inflation lumen through the rear opening of the inflation lumen.

10. The implantable device of claim 6, wherein the push wire lumen comprises the inlet being a rear opening at the conduit rear end and a front opening in fluid communication with the chamber of the adjustable membrane element for adjustably expanding or contracting the adjustable membrane element by a flowable material introduced through the rear opening, and further comprising:
a rear port connected to the conduit at the conduit rear end, the rear port including a cavity and an elastic septum configured to seal the cavity, the cavity configured to contain the flowable material and being in fluid communication with the inflation lumen through the rear opening of the push wire lumen.

11. An implantable device kit for controllable coaptation of a body lumen in tissue of a living body, comprising:
a hollow core push wire including a push wire front end, a push wire rear end, and a core lumen extending longitudinally in the push wire and having one or more front openings at the push wire front end and a rear opening at the push wire rear end; and
an implantable device configured to be positioned in the tissue adjacent to the body lumen using the push wire and to control the coaptation of the body lumen, the implantable device including:
an adjustable membrane element including a continuous wall having an inner surface defining a chamber;
an elongate conduit including a conduit peripheral surface, a conduit rear end, a conduit front end, and a push wire lumen, the conduit peripheral surface connected to and sealed to the adjustable membrane element at or near the conduit front end, the push wire lumen extending longitudinally in the conduit and having an inlet to receive a portion of the push wire and a diameter suitable for accommodating the received portion of the push wire; and
a fixation mechanism coupled to the conduit front end and configured to anchor the implantable device to a portion of the tissue to limit displacement of the implantable device in the tissue after the positioning by engaging a portion of the tissue using a forward longitudinal movement of the push wire and trapping the engaged portion of the tissue using a reverse longitudinal movement of the push wire, the forward longitudinal movement resulting from pushing the push wire toward the conduit front end, the reverse longitudinal movement being a longitudinal movement in a direction opposite to a direction of the forward longitudinal movement, and the one or more front openings of the core lumen of the push wire are positioned for facilitating the engagement of the portion of the tissue by drawing a fluid from the core lumen,
wherein the implantable device is configured for implantation within the tissue with the adjustable membrane element adjacent the body lumen to provide volume to the tissue for adjustable coaptation to the body lumen.

12. The implantable device kit of claim 11, wherein the fixation mechanism comprises a spring including a spring front end, a spring rear end coupled to the conduit front end, and a device tip coupled to the spring front end to be pushed by the forward longitudinal movement of the push wire for extending the spring, the spring is configured to be extended to engage the portion of the tissue using the forward longitudinal movement of and to contract to trap the engaged portion of the tissue using the reverse longitudinal movement of the push wire, and the one or more front openings of the core lumen of the push wire are positioned to facilitate the engagement of the portion of the tissue by drawing the fluid from the core lumen when the spring is extended.

13. A method for coapting a body lumen in tissue of a living body, the method comprising:
providing an implantable device including
an adjustable membrane element including a continuous wall having an inner surface defining a chamber;
an elongate conduit including a conduit peripheral surface, a conduit rear end, a conduit front end, and a push wire lumen, the conduit peripheral surface connected to and sealed to the adjustable membrane element at or near the conduit front end, the push wire lumen extending longitudinally in the conduit and having an inlet to receive a portion of a push wire and a diameter suitable for accommodating the received portion of the push wire; and a fixation mechanism including a spring and configured to anchor the implantable device to the tissue;

engaging a portion of the tissue by extending the spring using a forward longitudinal movement of the push wire resulting from pushing the push wire toward the conduit front end; and trapping the engaged portion of the tissue by returning the spring to a resting position using a reverse longitudinal movement of the push wire resulting from pulling the push wire in a direction opposite to a direction of the forward longitudinal movement, wherein the implantable device is configured for implantation within the tissue with the adjustable membrane element adjacent the body lumen to provide volume to the tissue for adjustable coaptation to the body lumen.

14. The method of claim 13, wherein operating the fixation mechanism comprises using one or more longitudinal movements of the push wire to activate the fixation mechanism for anchoring the implantable device to the tissue and additional one or more longitudinal movements of the push wire to deactivate the fixation mechanism for releasing the implantable device from the tissue.

15. The method of claim 13, wherein operating the fixation mechanism comprises using one or more longitudinal movements of the push wire to activate the fixation mechanism for anchoring the implantable device to the tissue and pulling the implantable device for releasing the implantable device from the tissue.

16. A method for coapting a body lumen in tissue of a living body, the method comprising:

providing an implantable device including an adjustable membrane element including a continuous wall having an inner surface defining a chamber;

an elongate conduit including a conduit peripheral surface, a conduit rear end, a conduit front end, and a push wire lumen, the conduit peripheral surface connected to and sealed to the adjustable membrane element at or near the conduit front end, the push wire lumen extending longitudinally in the conduit and having an inlet to receive a portion of a push wire and a diameter suitable for accommodating the received portion of the push wire; and a fixation mechanism including pincers and configured to anchor the implantable device to the tissue;

engaging a portion of the tissue by opening the pincers using a forward longitudinal movement of the push wire resulting from pushing the push wire toward the conduit front end; and trapping the engaged portion of the tissue by closing the pincers using a reverse longitudinal movement of the push wire resulting from pulling the push wire in a direction opposite to a direction of the forward longitudinal movement, wherein the implantable device is configured for implantation within the tissue with the adjustable membrane element adjacent the body lumen to provide volume to the tissue for adjustable coaptation to the body lumen.

17. The method of claim 16, wherein operating the fixation mechanism comprises using one or more longitudinal movements of the push wire to activate the fixation mechanism for anchoring the implantable device to the tissue and additional one or more longitudinal movements of the push wire to deactivate the fixation mechanism for releasing the implantable device from the tissue.

18. The method of claim 16, wherein operating the fixation mechanism comprises using one or more longitudinal movements of the push wire to activate the fixation mechanism for anchoring the implantable device to the tissue and pulling the implantable device for releasing the implantable device from the tissue.

19. A method for coapting a body lumen in tissue of a living body, the method comprising:

providing an implantable device including an adjustable membrane element including a continuous wall having an inner surface defining a chamber;

an elongate conduit including a conduit peripheral surface, a conduit rear end, a conduit front end, and a push wire lumen, the conduit peripheral surface connected to and sealed to the adjustable membrane element at or near the conduit front end, the push wire lumen extending longitudinally in the conduit and having an inlet to receive a portion of a push wire and a diameter suitable for accommodating the received portion of the push wire; and a fixation mechanism configured to anchor the implantable device to the tissue;

engaging a portion of the tissue using a forward longitudinal movement of the longitudinal movements of the push wire, the forward longitudinal movement resulting from pushing the push wire toward the conduit front end;

trapping the engaged portion of the tissue using a reverse longitudinal movement of the longitudinal movements of the push wire, the reverse longitudinal movement being a longitudinal movement in a direction opposite to a direction of the forward longitudinal movement: and passing a fluid through a lumen to facilitate the engagement of the portion of the tissue, the lumen including at least one of the push wire lumen of the conduit of the implantable device or a core lumen of the push wire, wherein the implantable device is configured for implantation within the tissue with the adjustable membrane element adjacent the body lumen to provide volume to the tissue for adjustable coaptation to the body lumen.

20. The method of claim 19, wherein operating the fixation mechanism comprises using one or more longitudinal movements of the push wire to activate the fixation mechanism for anchoring the implantable device to the tissue and additional one or more longitudinal movements of the push wire to deactivate the fixation mechanism for releasing the implantable device from the tissue.

21. The method of claim 19, wherein operating the fixation mechanism comprises using one or more longitudinal movements of the push wire to activate the fixation mechanism for anchoring the implantable device to the tissue and pulling the implantable device for releasing the implantable device from the tissue.

* * * * *